United States Patent
Huber et al.

(10) Patent No.: US 8,863,235 B2
(45) Date of Patent: Oct. 14, 2014

(54) TIME-DEPENDENT WHITE LIST GENERATION

(75) Inventors: Kurt Donald Huber, Kennesaw, GA (US); Judson John Flynn, Decatur, GA (US); William Gordon Mansfield, Sugar Hill, GA (US)

(73) Assignee: AT&T Mobility II LLC, Atlanta, GA (US)

( * ) Notice: Subject to any disclaimer, the term of this patent is extended or adjusted under 35 U.S.C. 154(b) by 615 days.

(21) Appl. No.: 12/275,416

(22) Filed: Nov. 21, 2008

(65) Prior Publication Data

US 2009/0288144 A1 Nov. 19, 2009

Related U.S. Application Data

(60) Provisional application No. 61/052,813, filed on May 13, 2008.

(51) Int. Cl.

| | |
|---|---|
| *H04L 29/06* | (2006.01) |
| *G06Q 30/02* | (2012.01) |
| *G06Q 20/32* | (2012.01) |
| *H04W 12/08* | (2009.01) |
| *G06Q 30/06* | (2012.01) |
| *H04W 48/16* | (2009.01) |
| *G06Q 20/12* | (2012.01) |
| *G06Q 20/40* | (2012.01) |
| *G06Q 20/38* | (2012.01) |
| *H04W 4/02* | (2009.01) |
| *H04W 48/20* | (2009.01) |
| *H04W 48/08* | (2009.01) |
| *H04W 84/04* | (2009.01) |

(52) U.S. Cl.
CPC ........... *H04W 48/16* (2013.01); *G06Q 30/0261* (2013.01); *G06Q 20/32* (2013.01); *H04L 63/101* (2013.01); *H04W 12/08* (2013.01); *G06Q 30/0601* (2013.01); *G06Q 20/3223* (2013.01); *H04W 84/045* (2013.01); *G06Q 20/1235* (2013.01); *H04L 2209/80* (2013.01); *G06Q 20/405* (2013.01); *G06Q 20/387* (2013.01); *G06Q 30/02* (2013.01); *H04W 4/02* (2013.01); *G06Q 20/322* (2013.01); *G06Q 30/0222* (2013.01); *H04W 48/20* (2013.01); *H04W 48/08* (2013.01)
USPC .............................................. 726/3; 713/168

(58) Field of Classification Search
CPC .. H04L 63/101; H04L 2209/80; H04W 12/08
USPC ............................................................ 726/3
See application file for complete search history.

(56) References Cited

U.S. PATENT DOCUMENTS

| | | |
|---|---|---|
| 5,745,559 A | 4/1998 | Weir |
| 5,864,764 A | 1/1999 | Thro et al. |

(Continued)

FOREIGN PATENT DOCUMENTS

| | | |
|---|---|---|
| CN | 1429005 A | 12/2001 |
| CN | 101017554 A | 8/2007 |

(Continued)

OTHER PUBLICATIONS

Ahmadullah et al., Video on Demand, Jun. 2004, Univeristy of Peshawar, pp. 1-21.*

(Continued)

*Primary Examiner* — Hadi Armouche
*Assistant Examiner* — Dao Ho
(74) *Attorney, Agent, or Firm* — Amin, Turocy & Watson, LLP

(57) ABSTRACT

A method is provided to control access to a femto cell. The method includes configuring one or more time-dependent parameters that specify access to a femto cell service. An access control list is employed for the femto cell service, where the access control list utilizes the time-dependent parameters to enable or deny access to the femto cell service. Access is granted to the femto cell service according to the access control list and the time-dependent parameters.

20 Claims, 16 Drawing Sheets

(56) References Cited

U.S. PATENT DOCUMENTS

| | | | |
|---|---|---|---|
| 6,052,594 A | 4/2000 | Chuang et al. | |
| 6,151,505 A | 11/2000 | Larkins | |
| 6,208,659 B1 | 3/2001 | Govindarajan et al. | |
| 6,219,786 B1* | 4/2001 | Cunningham et al. | 713/152 |
| 6,256,504 B1 | 7/2001 | Tell et al. | |
| 6,266,537 B1 | 7/2001 | Kashitani et al. | |
| 6,295,454 B1 | 9/2001 | Havinis et al. | |
| 6,363,261 B1 | 3/2002 | Raghavan | |
| 6,483,852 B1 | 11/2002 | Jacquet et al. | |
| 6,484,096 B2 | 11/2002 | Wong | |
| 6,512,478 B1 | 1/2003 | Chien | |
| 6,710,651 B2 | 3/2004 | Forrester | |
| 6,718,023 B1 | 4/2004 | Zolotov | |
| 6,768,722 B1 | 7/2004 | Katseff et al. | |
| 7,080,139 B1 | 7/2006 | Briggs et al. | |
| 7,142,861 B2 | 11/2006 | Murai | |
| 7,146,153 B2 | 12/2006 | Russell | |
| 7,209,739 B1 | 4/2007 | Narayanabhatla | |
| 7,277,410 B2 | 10/2007 | Horneman | |
| 7,317,931 B2 | 1/2008 | Guo | |
| 7,370,356 B1 | 5/2008 | Guo | |
| 7,437,755 B2 | 10/2008 | Farino et al. | |
| 7,493,390 B2 | 2/2009 | Bobde et al. | |
| 7,496,383 B2 | 2/2009 | Kurata | |
| 7,509,124 B2 | 3/2009 | O'Neil | |
| 7,516,219 B2 | 4/2009 | Moghaddam et al. | |
| 7,558,251 B1 | 7/2009 | Huang et al. | |
| 7,574,731 B2 | 8/2009 | Fascenda et al. | |
| 7,613,444 B2 | 11/2009 | Lindqvist et al. | |
| 7,614,078 B1 | 11/2009 | Stieglitz et al. | |
| 7,623,857 B1 | 11/2009 | O'Neil | |
| 7,633,910 B2 | 12/2009 | Zhun et al. | |
| 7,751,826 B2 | 7/2010 | Gardner | |
| 7,761,526 B2 | 7/2010 | Pounds et al. | |
| 7,768,983 B2 | 8/2010 | Nylander et al. | |
| 7,853,265 B1 | 12/2010 | Ahmad et al. | |
| 7,885,644 B2 | 2/2011 | Gallagher et al. | |
| 7,929,537 B2 | 4/2011 | Vasudevan et al. | |
| 7,929,970 B1 | 4/2011 | Gunasekara | |
| 7,941,144 B2 | 5/2011 | Nylander et al. | |
| 7,995,994 B2 | 8/2011 | Khetawat et al. | |
| 8,064,909 B2 | 11/2011 | Spinelli et al. | |
| 8,103,285 B2 | 1/2012 | Kalhan | |
| 8,108,923 B1 | 1/2012 | Satish et al. | |
| 8,265,685 B2 | 9/2012 | Vikberg et al. | |
| 8,437,745 B2 | 5/2013 | Theppasandra et al. | |
| 8,509,778 B2 | 8/2013 | Buchmayer et al. | |
| 8,743,776 B2 | 6/2014 | Gurajala et al. | |
| 2002/0044639 A1 | 4/2002 | Shioda et al. | |
| 2002/0077115 A1 | 6/2002 | Ruutu et al. | |
| 2002/0098837 A1 | 7/2002 | Ferrario et al. | |
| 2002/0107018 A1 | 8/2002 | Nakamura et al. | |
| 2002/0123365 A1 | 9/2002 | Thorson | |
| 2002/0142791 A1 | 10/2002 | Chen et al. | |
| 2003/0028621 A1 | 2/2003 | Furlong et al. | |
| 2003/0109271 A1 | 6/2003 | Lewis et al. | |
| 2003/0125044 A1 | 7/2003 | Deloach | |
| 2003/0133558 A1 | 7/2003 | Kung et al. | |
| 2003/0139180 A1 | 7/2003 | McIntosh et al. | |
| 2003/0142637 A1 | 7/2003 | Khawer et al. | |
| 2003/0144793 A1 | 7/2003 | Melaku et al. | |
| 2003/0153302 A1 | 8/2003 | Lewis et al. | |
| 2004/0111382 A1* | 6/2004 | Haji-Ioannou | 705/400 |
| 2004/0125781 A1 | 7/2004 | Walter et al. | |
| 2004/0203846 A1 | 10/2004 | Caronni et al. | |
| 2004/0235455 A1 | 11/2004 | Jiang | |
| 2004/0236702 A1 | 11/2004 | Fink et al. | |
| 2004/0258003 A1 | 12/2004 | Kotot et al. | |
| 2004/0264428 A1* | 12/2004 | Choi et al. | 370/338 |
| 2005/0003797 A1 | 1/2005 | Baldwin | |
| 2005/0009499 A1 | 1/2005 | Koster | |
| 2005/0024201 A1 | 2/2005 | Culpepper et al. | |
| 2005/0026650 A1 | 2/2005 | Russell | |
| 2005/0075114 A1 | 4/2005 | Dennison et al. | |
| 2005/0108529 A1 | 5/2005 | Juneau | |
| 2005/0144279 A1 | 6/2005 | Wexelblat | |
| 2005/0160276 A1* | 7/2005 | Braun et al. | 713/185 |
| 2005/0172148 A1 | 8/2005 | Ying | |
| 2005/0177645 A1 | 8/2005 | Dowling et al. | |
| 2005/0223389 A1 | 10/2005 | Klein et al. | |
| 2005/0239448 A1 | 10/2005 | Bayne | |
| 2005/0250527 A1 | 11/2005 | Jugl | |
| 2005/0254451 A1 | 11/2005 | Grosbach | |
| 2005/0255893 A1 | 11/2005 | Jin et al. | |
| 2005/0259654 A1 | 11/2005 | Faulk, Jr. | |
| 2005/0269402 A1 | 12/2005 | Spitzer et al. | |
| 2005/0283518 A1* | 12/2005 | Sargent | 709/201 |
| 2006/0031387 A1 | 2/2006 | Hamzeh et al. | |
| 2006/0031493 A1 | 2/2006 | Cugi | |
| 2006/0046647 A1 | 3/2006 | Parikh et al. | |
| 2006/0074814 A1 | 4/2006 | Lovell et al. | |
| 2006/0075098 A1 | 4/2006 | Becker et al. | |
| 2006/0182074 A1 | 8/2006 | Kubler et al. | |
| 2006/0223498 A1 | 10/2006 | Gallagher et al. | |
| 2006/0244589 A1 | 11/2006 | Schranz | |
| 2006/0281457 A1 | 12/2006 | Huotari et al. | |
| 2007/0002844 A1 | 1/2007 | Ali | |
| 2007/0008894 A1 | 1/2007 | Lynch et al. | |
| 2007/0025245 A1 | 2/2007 | Porras et al. | |
| 2007/0032225 A1 | 2/2007 | Konicek et al. | |
| 2007/0032269 A1 | 2/2007 | Shostak | |
| 2007/0066318 A1 | 3/2007 | Danzeisen et al. | |
| 2007/0074272 A1* | 3/2007 | Watanabe | 726/3 |
| 2007/0094601 A1 | 4/2007 | Greenberg et al. | |
| 2007/0097093 A1 | 5/2007 | Ohshita et al. | |
| 2007/0097938 A1 | 5/2007 | Nylander et al. | |
| 2007/0097939 A1 | 5/2007 | Nylander et al. | |
| 2007/0097983 A1 | 5/2007 | Nylander et al. | |
| 2007/0099561 A1 | 5/2007 | Voss | |
| 2007/0104166 A1 | 5/2007 | Rahman et al. | |
| 2007/0111706 A1 | 5/2007 | Kumar et al. | |
| 2007/0123253 A1 | 5/2007 | Simongini et al. | |
| 2007/0124802 A1 | 5/2007 | Anton et al. | |
| 2007/0133563 A1* | 6/2007 | Hundscheidt et al. | 370/395.43 |
| 2007/0150732 A1 | 6/2007 | Suzuki et al. | |
| 2007/0155421 A1 | 7/2007 | Alberth et al. | |
| 2007/0167175 A1 | 7/2007 | Wong | |
| 2007/0183427 A1* | 8/2007 | Nylander et al. | 370/395.2 |
| 2007/0184815 A1 | 8/2007 | Aebi | |
| 2007/0199076 A1 | 8/2007 | Rensin et al. | |
| 2007/0220252 A1 | 9/2007 | Sinko et al. | |
| 2007/0232332 A1 | 10/2007 | Holur et al. | |
| 2007/0258418 A1 | 11/2007 | Wurtenberger et al. | |
| 2007/0270152 A1 | 11/2007 | Nylander et al. | |
| 2007/0275739 A1 | 11/2007 | Blackburn | |
| 2007/0287501 A1 | 12/2007 | Hoshina | |
| 2008/0043972 A1 | 2/2008 | Ruetschi et al. | |
| 2008/0049702 A1 | 2/2008 | Meylan et al. | |
| 2008/0065752 A1 | 3/2008 | Ch'ng et al. | |
| 2008/0076392 A1 | 3/2008 | Khetawat et al. | |
| 2008/0076393 A1 | 3/2008 | Khetawat et al. | |
| 2008/0076398 A1 | 3/2008 | Mate et al. | |
| 2008/0076412 A1 | 3/2008 | Khetawat et al. | |
| 2008/0076419 A1 | 3/2008 | Khetawat et al. | |
| 2008/0076420 A1 | 3/2008 | Khetawat et al. | |
| 2008/0076425 A1 | 3/2008 | Khetawat et al. | |
| 2008/0081636 A1 | 4/2008 | Nylander et al. | |
| 2008/0082538 A1 | 4/2008 | Meijer et al. | |
| 2008/0119160 A1 | 5/2008 | Andriantsiferana et al. | |
| 2008/0126531 A1 | 5/2008 | Setia et al. | |
| 2008/0132239 A1 | 6/2008 | Khetawat et al. | |
| 2008/0133742 A1 | 6/2008 | Southiere et al. | |
| 2008/0141348 A1 | 6/2008 | Hovnanian et al. | |
| 2008/0151807 A1 | 6/2008 | Meier et al. | |
| 2008/0168099 A1 | 7/2008 | Skaf | |
| 2008/0181184 A1 | 7/2008 | Kezys | |
| 2008/0201076 A1 | 8/2008 | Huang et al. | |
| 2008/0207170 A1 | 8/2008 | Khetawat et al. | |
| 2008/0242280 A1 | 10/2008 | Shapiro et al. | |
| 2008/0244148 A1 | 10/2008 | Nix et al. | |
| 2008/0254792 A1 | 10/2008 | Ch'ng | |
| 2008/0261602 A1 | 10/2008 | Livneh et al. | |
| 2008/0274753 A1 | 11/2008 | Attar et al. | |
| 2008/0281687 A1 | 11/2008 | Hurwitz et al. | |

(56) References Cited

U.S. PATENT DOCUMENTS

| | | |
|---|---|---|
| 2008/0282327 A1 | 11/2008 | Winget et al. |
| 2008/0299984 A1 | 12/2008 | Shimomura |
| 2008/0299992 A1 | 12/2008 | Eitan et al. |
| 2008/0305792 A1 | 12/2008 | Khetawat et al. |
| 2008/0305801 A1 | 12/2008 | Burgess et al. |
| 2008/0305834 A1 | 12/2008 | Janiszewski et al. |
| 2008/0318551 A1 | 12/2008 | Palamara et al. |
| 2009/0012898 A1 | 1/2009 | Sharma et al. |
| 2009/0031006 A1 | 1/2009 | Johnson et al. |
| 2009/0037973 A1 | 2/2009 | Gustave et al. |
| 2009/0042593 A1 | 2/2009 | Yavuz et al. |
| 2009/0046665 A1 | 2/2009 | Robson et al. |
| 2009/0047945 A1 | 2/2009 | Zhang |
| 2009/0059822 A1 | 3/2009 | Morrill et al. |
| 2009/0061821 A1 | 3/2009 | Chen et al. |
| 2009/0061873 A1 | 3/2009 | Bao et al. |
| 2009/0077620 A1 | 3/2009 | Ravi et al. |
| 2009/0082010 A1 | 3/2009 | Lee |
| 2009/0082020 A1 | 3/2009 | Ch'ng et al. |
| 2009/0092080 A1 | 4/2009 | Balasubramanian et al. |
| 2009/0092081 A1 | 4/2009 | Balasubramanian et al. |
| 2009/0092096 A1 | 4/2009 | Czaja |
| 2009/0092097 A1 | 4/2009 | Nylander et al. |
| 2009/0093232 A1 | 4/2009 | Gupta et al. |
| 2009/0094351 A1 | 4/2009 | Gupta et al. |
| 2009/0094680 A1 | 4/2009 | Gupta et al. |
| 2009/0097436 A1 | 4/2009 | Vasudevan et al. |
| 2009/0098871 A1 | 4/2009 | Gogic |
| 2009/0111499 A1 | 4/2009 | Bosch |
| 2009/0122773 A1 | 5/2009 | Gogic |
| 2009/0124262 A1 | 5/2009 | Vela et al. |
| 2009/0129336 A1 | 5/2009 | Osborn et al. |
| 2009/0129350 A1 | 5/2009 | Khandekar et al. |
| 2009/0131050 A1 | 5/2009 | Osborn |
| 2009/0131098 A1 | 5/2009 | Khandekar et al. |
| 2009/0135749 A1 | 5/2009 | Yang |
| 2009/0135794 A1 | 5/2009 | Su et al. |
| 2009/0156213 A1 | 6/2009 | Spinelli et al. |
| 2009/0161682 A1 | 6/2009 | Johnson et al. |
| 2009/0163216 A1 | 6/2009 | Hoang et al. |
| 2009/0163224 A1 | 6/2009 | Dean |
| 2009/0164547 A1* | 6/2009 | Ch'ng et al. .................. 709/201 |
| 2009/0170440 A1 | 7/2009 | Eyuboglu et al. |
| 2009/0170528 A1 | 7/2009 | Bull et al. |
| 2009/0180428 A1 | 7/2009 | Viswanath |
| 2009/0191844 A1 | 7/2009 | Morgan et al. |
| 2009/0191845 A1 | 7/2009 | Morgan et al. |
| 2009/0210324 A1 | 8/2009 | Bhogal |
| 2009/0213825 A1 | 8/2009 | Gupta et al. |
| 2009/0215429 A1 | 8/2009 | Caldwell et al. |
| 2009/0215452 A1 | 8/2009 | Balasubramanian et al. |
| 2009/0221303 A1 | 9/2009 | Soliman |
| 2009/0233574 A1 | 9/2009 | Shinozaki |
| 2009/0245176 A1 | 10/2009 | Balasubramanian et al. |
| 2009/0247157 A1 | 10/2009 | Yoon et al. |
| 2009/0253421 A1 | 10/2009 | Camp et al. |
| 2009/0253432 A1 | 10/2009 | Willey et al. |
| 2009/0257434 A1 | 10/2009 | Song et al. |
| 2009/0279701 A1 | 11/2009 | Moisand et al. |
| 2009/0291667 A1 | 11/2009 | Vakil et al. |
| 2009/0325634 A1 | 12/2009 | Bienas et al. |
| 2010/0022266 A1 | 1/2010 | Villier |
| 2010/0040026 A1 | 2/2010 | Melkesetian |
| 2010/0048165 A1 | 2/2010 | Caldwell et al. |
| 2010/0113067 A1 | 5/2010 | Fullam et al. |
| 2010/0167777 A1 | 7/2010 | Raghothaman et al. |
| 2010/0260068 A1 | 10/2010 | Bhatt et al. |
| 2011/0177794 A1 | 7/2011 | Nylander et al. |
| 2011/0200022 A1 | 8/2011 | Annamalai |
| 2011/0280154 A1 | 11/2011 | Silverstrim et al. |
| 2012/0258711 A1 | 10/2012 | Bao et al. |
| 2013/0165079 A1 | 6/2013 | Gogic |

FOREIGN PATENT DOCUMENTS

| | | |
|---|---|---|
| CN | 101175333 A | 5/2008 |
| GB | 2425291 A | 10/2006 |
| GB | 2425921 A | 11/2006 |
| JP | 20010264096 | 9/2001 |
| JP | 2003022303 | 1/2003 |
| JP | 2003288521 | 10/2003 |
| JP | 2004112324 | 4/2004 |
| JP | 2005073147 | 3/2005 |
| JP | 2005215849 | 8/2005 |
| JP | 2006067143 | 3/2006 |
| JP | 2008048055 | 2/2008 |
| WO | WO 0214987 A2 * | 2/2002 |
| WO | 2005076964 A2 | 8/2005 |
| WO | 2007015067 A2 | 2/2007 |
| WO | 2007040449 A1 | 4/2007 |
| WO | 2008047039 A1 | 4/2008 |

OTHER PUBLICATIONS

International Search Report and Written Opinion mailed Feb. 23, 2010, for PCT Application No. PCT/US2009/043846, 13 pages.
OA dated Dec. 31, 2009 for U.S. Appl No. 11/457,129, 16 pages.
OA dated Apr. 17, 2009 for U.S. Appl. No. 11/276,269, 15 pages.
OA dated Nov. 4, 2008 for U.S. Appl. No. 11/276,269, 15 pages.
OA dated Mar. 29, 2011 for U.S. Appl. No. 12/276,002, 37 pages.
OA dated Apr. 13, 2011 for U.S. Appl. No. 12/276,058, 40 pages.
OA dated Apr. 19, 2011 for U.S. Appl. No. 12/276,238, 22 pages.
OA dated May 5, 2011 for U.S. Appl. No. 12/275,015, 32 pages.
OA dated Jun. 14, 2011 for U.S. Appl. No. 12/275,878, 35 pages.
OA dated Jun. 22, 2011 for U.S. Appl. No. 12/484,072, 38 pages.
OA dated Jul. 7, 2011 for U.S. Appl. No. 12/276,257, 24 pages.
OA dated Jun. 28, 2011 for U.S. Appl. No. 12/275,925, 18 pages.
OA dated Jun. 8, 2011 for U.S. Appl. No. 12/484,026, 30 pages.
International Search Report and Written Opinion dated Oct. 27, 2009 for PCT Application Serial No. PCT/US2009/043861, 14 Pages.
OA dated Jun. 17, 2010 for U.S. Appl. No. 11/457,129, 15 pages.
Kaul, "Verizon's $250 femto box—A deliberate ploy behind the aggressive pricing?" Posted Tue, Jan. 20, 2009 13:19:46 EST; http://www.abiresearch.com/research_blog/569; © 2009 Allied Business Intelligence, Inc.
OA dated Jul. 21, 2011 for U.S. Appl. No. 12/175,293, 30 pages.
OA dated Sep. 14, 2011 for U.S. Appl. No. 12/276,002, 35 pages.
OA dated Oct. 5, 2011 for U.S. Appl. No. 12/276,058, 37 pages.
OA dated Oct. 6, 2011 for U.S. Appl. No. 12/465,483, 50 pages.
OA dated Oct. 4, 2011 for U.S. Appl. No. 12/484,135, 44 pages.
OA dated Oct. 24, 2011 for U.S. Appl. No. 12/275,925, 14 pages.
OA dated Nov. 30, 2011 for U.S. Appl. No. 12/275,878, 38 pages.
OA dated Dec. 1, 2011 for U.S. Appl. No. 12/275,996, 44 pages.
OA dated Oct. 25, 2011 for U.S. Appl. No. 12/465,580, 39 pages.
OA dated Nov. 8, 2011 for U.S. Appl. No. 12/465,468, 50 pages.
OA dated Jan. 5, 2012 for U.S. Appl. No. 12/465,585, 43 pages.
OA dated Dec. 28, 2011 for U.S. Appl. No. 12/175,293, 38 pages.
OA dated Nov. 21, 2011 for U.S. Appl. No. 12/484,026, 37 pages.
OA dated Dec. 14, 2011 for U.S. Appl. No. 12/484,072, 44 pages.
OA dated Nov. 1, 2011 for U.S. Appl. No. 12/816,087, 33 pages.
OA dated Jul. 16, 2012 for U.S. Appl. No. 12/275,878, 37 pages.
OA dated Jul. 10, 2012 for U.S. Appl. No. 12/465,585, 32 pages.
OA dated Sep. 5, 2012 for U.S. Appl. No. 12/276,120, 49 pages.
OA dated Aug. 16, 2012 for U.S. Appl. No. 12/465,598, 31 pages.
OA dated Sep. 6, 2012 for U.S. Appl. No. 12/579,957, 51 pages.
OA dated Sep. 10, 2012 for U.S. Appl. No. 12/276,002, 54 pages.
OA dated Mar. 5, 2012 for U.S. Appl. No. 12/465,598, 55 pages.
OA dated Mar. 19, 2012 for U.S. Appl. No. 12/276,120, 68 pages.
OA dated Mar. 30, 2012 for U.S. Appl. No. 12/484,026, 30 pages.
Notice of Allowance dated Apr. 3, 2012 for U.S. Appl. No. 12/275,996, 38 pages.
OA dated May 8, 2012 for U.S. Appl. No. 11/457,129, 38 pages.
OA dated Apr. 10, 2012 for U.S. Appl. No. 12/484,135, 45 pages.
OA dated Apr. 13, 2012 for U.S. Appl. No. 13/316,106, 35 pages.
Notice of Allowance dated Apr. 25, 2012 for U.S. Appl. No. 12/465,468, 35 pages.

(56) References Cited

OTHER PUBLICATIONS

Office Action dated Jan. 17, 2013 for U.S. Appl. No. 13/554,710, 42 pages.
Final OA dated Feb. 15, 2013 for U.S. Appl. No. 12/579,957.
OA dated Feb. 26, 2013 for U.S. Appl. No. 12/276,120, 59 pages.
Final OA dated Mar. 14, 2013 for U.S. Appl. No. 12/484,072, 34 pages.
OA dated Oct. 2, 2012 for U.S. Appl. No. 12/484,026, 29 pages.
OA dated Oct. 11, 2012 for U.S. Appl. No. 13/487,794, 45 pages.
OA dated Oct. 9, 2012 for U.S. Appl. No. 13/298,924, 51 pages.
OA dated Nov. 1, 2012 for U.S. Appl. No. 12/276,058, 59 pages.
OA dated Nov. 5, 2012 for U.S. Appl. No. 12/484,072, 52 pages.
OA dated Nov. 20, 2012 for U.S. Appl. No. 12/275,878, 28 pages.
Japanese Office Action mailed Sep. 13, 2012 for Japanese Patent Application No. 2011-509669, 10 pages.
Canadian Office Action mailed Oct. 30, 2012 for Canadian Patent Application No. 2,722,324, 3 pages.
Japanese Office Action mailed Sep. 13, 2012 for Japanese Patent Application 2011-509675, 4 pages.
Office Action dated Apr. 23, 2013 for U.S. Appl. No. 12/175,293, 41 pages.
Canadian Office Action mailed Mar. 26, 2013 for Canadian Patent Application No. 2,722,324, 4 pages.
Office Action dated Jul. 15, 2013 for U.S. Appl. No. 13/554,710, 37 pages.
Office Action dated Dec. 12, 2013 for U.S. Appl. No. 12/276,120, 78 pages.
Notice of Allowance dated Feb. 13, 2014 for U.S. Appl. No. 12/275,878, 34 pages.
Hasan, Mohammad Masud; Huang, Xiadong; Jue, Jason P.; "Survivable Wireless Access Network Design with Dual-homing Capabilities"; IEEE Global Telecommunications Conference, Nov. 27-Dec. 1, 2006, 5 pgs.
Japanese Office Action dated Jan. 16, 2014 for Japanese Patent Application No. 2013-026198, 8 pages.
Office Action dated Aug. 13, 2013 for U.S. Appl. No. 121276,120, 66 pages.
Office Action dated Sep. 9, 2013 for U.S. Appl. No. 12/465,585, 45 pages.
Office Action dated Oct. 3, 2013 for U.S. Appl. No. 13/892,923, 62 pages.
Office Action dated Oct. 22, 2013 for US Application No. 13/898,910, 50 pages.
Office Action dated Oct. 3, 2013 for U.S. Appl. No. 13/934,644, 17 pages.
Chinese Office Action dated Oct. 24, 1013 for Chinese Patent Application No. 200980117263.8, 13 pages.
Chinese Office Action dated Oct. 21, 2013 for Chinese Patent Application No. 200980117188.5, 11 pages.
Japanese Office Action dated Oct. 3, 2013 for Japanese Patent Application No. 2011-509669, 15 pages.
Office Action dated Oct. 2, 2013 for U.S. Appl. No. 12/275,878, 38 pages.
Final Office Action dated Mar. 26, 2014 for U.S. Appl. No. 12/465,585, 44 pages.
Office Action dated Mar. 24, 2014 for U.S. Appl. No. 13/934,644, 50 pages.
Notice of Allowance dated Apr. 4, 2014 for U.S. Appl. No. 14/090,802, 63 pages.
Office Action dated Mar. 24, 2014 for U.S. Appl. No. 13/671,191, 63 pages.
Office Action dated Jun. 11, 2014 for U.S. Appl. No. 13/675,150, 68 Pages.
Office Action dated Jun. 9, 2014 for U.S. Appl. No. 12/276,120, 92 Pages.
Chinese Office Action dated Jun. 19, 2014 for Chinese Patent Application No. 200980117188.5, 5 Pages.
Canadian Office Action dated May 13, 2014 for Canadian Patent Application 2,722,367, 5 Pages.
Office Action dated Jun. 10, 2014 for U.S. Appl. No. 14/253,553, 16 pages.

* cited by examiner

TIME-DEPENDENT WHITE LIST GENERATION

CROSS-REFERENCE TO RELATED APPLICATION

This application claims the benefit of U.S. Provisional Patent application Ser. No. 61/052,813 entitled "MANAGEMENT OF ACCESS TO FEMTO CELL COVERAGE" and filed on May 13, 2008. The entirety of the above-referenced application is incorporated by reference herein.

TECHNICAL FIELD

The subject innovation relates to wireless communications and, more particularly, to management of access to femto cell coverage by a subscriber and subscriber stations where time-dependent lists are employed to access the femto cell.

BACKGROUND

Femto cells—building-based wireless access points interfaced with a wired broadband network—are generally deployed to improve indoor wireless coverage provided by a wireless network operator. Femto cells typically operate in licensed portions of the electromagnetic spectrum, and generally offer plug-and-play installation; e.g., automatic configuration of femto access point. Improved indoor coverage includes stronger signal and improved reception (e.g., voice or sound), ease of session or call initiation and session or call retention as well. Coverage of a femto cell, or femto AP, is intended to be confined within the bounds of an indoor compound, in order to mitigate interference among mobile stations covered by a macro cell and terminals covered by the femto AP. Additionally, confined coverage can reduce cross-talk among terminals serviced by disparate, neighboring femto cells as well.

Coverage improvements via femto cells can also mitigate customer attrition as long as a favorable subscriber perception regarding voice coverage and other data services with substantive delay sensitivity is attained. A positive customer experience can depend on adequate access management to femto cell service. One issue facing femto cell service relates to managing access to the cell. For instance, in a home cell, how does one prevent neighbors or other users from inadvertent or improper access to the cell. One aspect is through encrypted passwords or other security means to access the cell. One drawback to this technique is that it is difficult to allow a certain class of users access to the cell while restricting a broader range of users. Thus, current systems may require users to share passwords or other security credentials in order to allow access for specified reasons. As can be appreciated, sharing security credentials is likely to reduce the overall security of the system since more than one user now can potentially compromise the system.

SUMMARY

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

Systems and methods are provided to control access to femto cell service through access control list(s), or "white list(s)." Such white list(s) can be configured via a networked interface which facilitates access management to a femto cell. In one aspect, time-dependent parameters are configured via the interface to enable a certain class of users to have access during designated periods or time intervals. For example, a home cell may have a white list configured to allow a maintenance user to have access during a specified time period when the user is at the home working to solve a problem. In a business application, employees may be enabled to access a cell during their normal working hours or for other specified periods of time. Access can also be changed for differing levels of security in view of the particular time that has been configured. Access can be dynamically monitored and changed over time based upon determined patterns of usage. Typical time-dependent parameters include time of day, calendar periods, user id's, event descriptors, access type, modality employed, or application type. Other parameters can include designated constraints that may apply for a given access. White lists can include a set of subscriber station(s) identifier numbers, codes or tokens, and can also include additional fields for femto cell access management based on desired complexity. Various example aspects such as white list management, maintenance and dissemination; pre-configuration; and inclusion of wireless devices or subscribers can be provided.

To the accomplishment of the foregoing and related ends, the invention, then, comprises the features hereinafter fully described. The following description and the annexed drawings set forth in detail certain illustrative aspects of the invention. However, these aspects are indicative of but a few of the various ways in which the principles of the invention may be employed. Other aspects, advantages and novel features of the invention will become apparent from the following detailed description of the invention when considered in conjunction with the drawings.

DETAILED DESCRIPTION

Systems and methods are provided for controlling access to a femto cell service in view of one or more time-dependent parameters. In one aspect, a method is provided to control access to a femto cell. The method includes configuring one or more time-dependent parameters that specify access to a femto cell service. An access control list is employed for the femto cell service, where the access control list utilizes the time-dependent parameters to enable or deny access to the femto cell service. Access is granted to the femto cell service according to the access control list and the time-dependent parameters. The systems and methods can also include dynamically adjusting the time-dependent parameters by monitoring the femto cell service.

As used in this application, the terms "component," "system," "platform," "list," and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers. Also, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). Furthermore, the terms "user," "subscriber," "customer," "consumer," "prosumer," "agent," and the like are employed interchangeably throughout the subject specification, unless context warrants particular distinction(s) among the terms. As utilized herein, the term "prosumer" indicate the following contractions: professional-consumer and producer-consumer.

Figure 1:
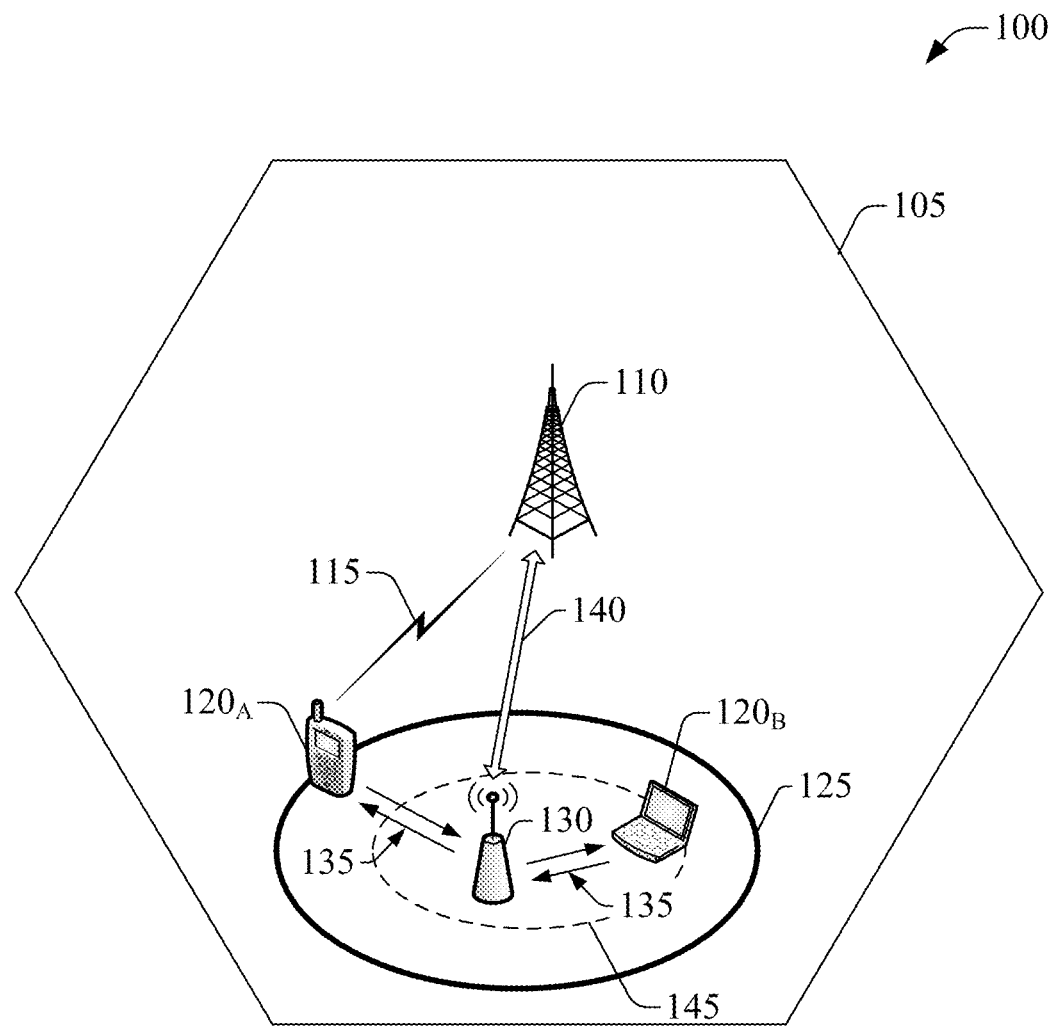
FIG. 1 a schematic deployment of a macro cell and a femto cell for wireless coverage in accordance with aspects described herein.

Referring initially to FIG. 1, a wireless environment (e.g., a network) 100 in which a femto cell is controlled in accordance with time-dependent white-lists which are described in more detail below with respect to FIGS. 2-5. In wireless environment 100, area 105 represents a coverage macro cell which is served by base station 110. Macro coverage is generally intended for outdoors locations for servicing mobile wireless devices, like UE $120_A$, and such coverage is achieved via a wireless link 115. In an aspect, UE 120 can be a 3GPP Universal Mobile Telecommunication System (UMTS) mobile phone.

Within macro coverage cell 105, a femto cell 145, served by a femto access point 130, can be deployed. A femto cell typically covers an area 125 that is determined, at least in part, by transmission power allocated to femto AP 130, path loss, shadowing, and so forth. Coverage area typically is spanned by a coverage radius that ranges from 20 to 50 meters. Confined coverage area 145 is generally associated with an indoors area, or a building, which can span about 5000 sq. ft. Generally, femto AP 130 typically services a few wireless devices (e.g., subscriber station $120_B$) within confined coverage area 145. In an aspect, femto AP 130 can integrate seamlessly with substantially any PS-based and CS-based network; for instance, femto AP 130 can integrate into an existing 3GPP Core via conventional interfaces like Iu-CS, Iu-PS, Gi, Gn. In another aspect, femto AP 130 can exploit high-speed downlink packet access in order to accomplish substantive bitrates. In yet another aspect, femto AP 130 has a LAC (location area code) and RAC (routing area code) that is different than the underlying macro network. These LAC and RAC are used to identify subscriber station location for a variety of reasons, most notably to direct incoming voice and data traffic to appropriate paging transmitters.

As a subscriber station, e.g., UE $120_A$, leaves macro coverage (e.g., cell 105) and enters femto coverage (e.g., area 125), as illustrated in environment 100, UE $120_A$ attempts to attach to the femto AP 130 through transmission and reception of attachment signaling, effected via a FL/RL 135; in an aspect, the attachment signaling can include a Location Area Update (LAU) and/or Routing Area Update (RAU). Attachment attempts are a part of procedures to ensure mobility, so voice calls and sessions can continue even after a macro-to-femto transition or vice versa. It is to be noted that UE 120 can be employed seamlessly after either of the foregoing transitions. Femto networks are also designed to serve stationary or slow-moving traffic with reduced signaling loads compared to macro networks. A femto service provider (e.g., an entity that commercializes, deploys, and/or utilizes femto access point 130) is therefore inclined to minimize unnecessary LAU/RAU signaling activity at substantially any opportunity to do so, and through substantially any available means. It is to be noted that substantially any mitigation of unnecessary attachment signaling/control is advantageous for femto cell operation. Conversely, if not successful, UE 120 is generally commanded (through a variety of communication means) to select another LAC/RAC or enter "emergency calls only" mode. It is to be appreciated that this attempt and handling process can occupy significant UE battery, and femto AP capacity and signaling resources as well.

When an attachment attempt is successful, UE 120 is allowed on femto cell 125 and incoming voice and data traffic are paged and routed to the subscriber through the femto AP 130. It is to be noted also that data traffic is typically routed through a backhaul broadband wired network backbone 140

(e.g., optical fiber backbone, twisted-pair line, T1/E1 phone line, DSL, or coaxial cable). To this end, femto AP 130 is connected to the broadband backhaul network backbone 140 via a broadband modem (not shown).

It is to be noted that as a femto AP 130 generally relies on a backhaul network backbone 140 for routing and paging, and for packet communication, substantially any quality of service handles heterogeneous packetized traffic. Namely, packet flows established for wireless devices (like terminals 120$_A$ and 120$_B$) served by femto AP 130, and for devices served through the backhaul network pipe 140. It is to be noted that to ensure a positive subscriber experience, or perception, it is important for femto AP 130 to maintain a high level of throughput for traffic (e.g., voice and data) utilized on a mobile device for one or more subscribers while in the presence of external, additional packetized, or broadband, traffic associated with applications (web browsing, data transfer (e.g., content upload), and the like) executed in devices within the femto coverage area (e.g., either area 125 or area 145).

Figure 2:
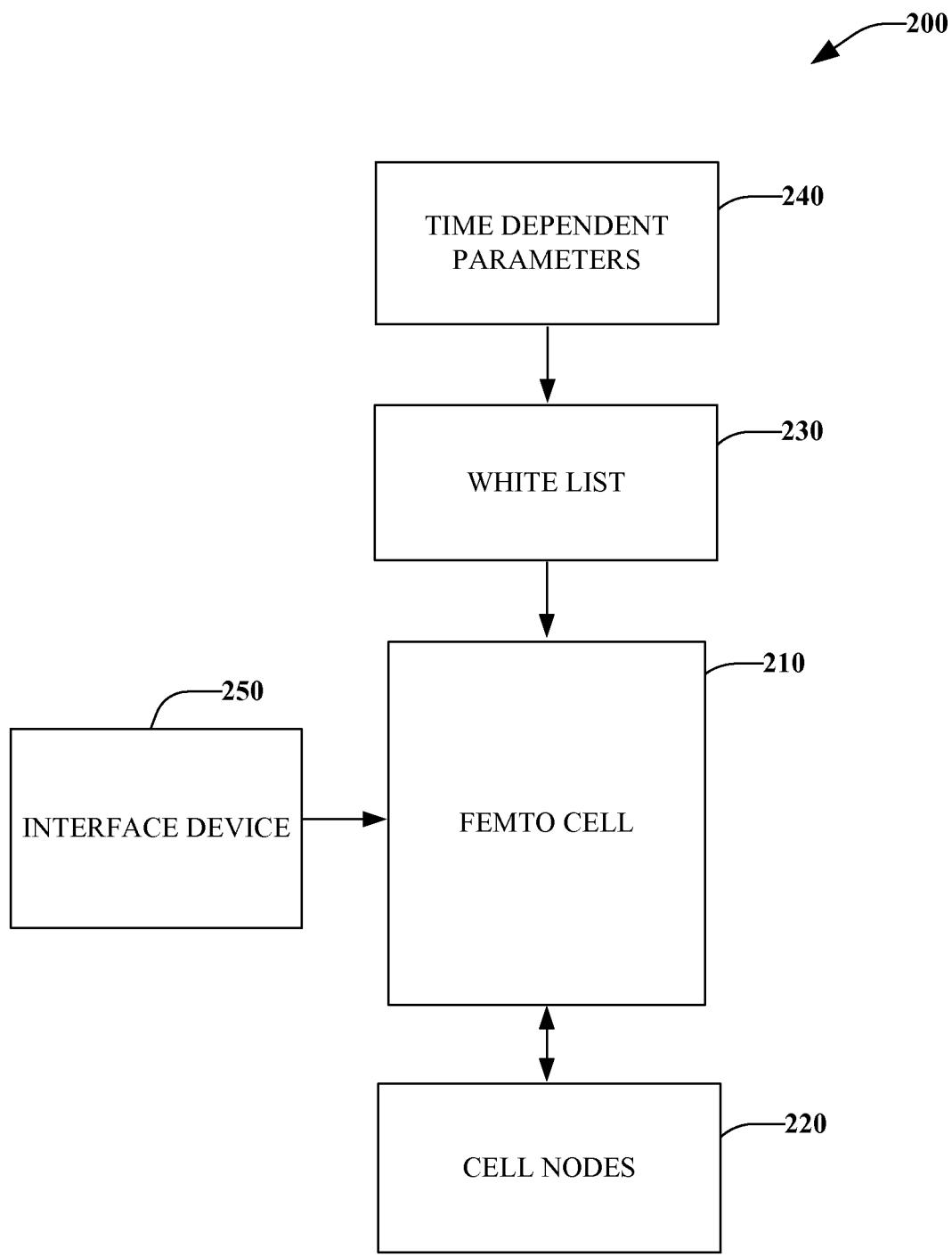
FIG. 2 is a block diagram of a system that employs time-dependent parameters in accordance with a white list for femto cell access.

FIG. 2 is a block diagram of a system that employs time-dependent parameters in accordance with a white list for femto cell access. The system 200 includes a femto cell 210 (or cells) that communicate to one or more cell nodes 220, wherein such nodes can include devices, software components, or combinations thereof that enable data exchange with the cell. A white list 230 is employed to control access to the femto cell 210. For instance, the white list 230 can electronically specify who or what devices can be enabled to communicate with the cell 210 and nodes 220. This can include disabling access if one or more conditions of the list 230 are not satisfied. One type of condition that can be employed with the white list 230 includes one or more time dependent parameters 240 that operate as enabling or disabling conditions that control access of an interface device(s) 250 to the femto cell 210. The time dependent parameters 240 specify periods of time or other time-related occurrences that allow users and their respective devices 250 to send or receive data (or otherwise communicate) to the femto cell 210.

In one aspect, white list time parameters are provided that control utilization logic of white list(s) content include, without being limited to including: (i) temporary access, e.g., full access for a specific time interval such as days or hours; (ii) access only within a window of time in a day (voice and data allowed from 9:00 a-6:00 p, or voice allowed after 9:00 p which can facilitate billing schemes already established by an operator/service provider); and (iii) access to specific applications such as scheduler, calendar(s), news streaming, authoring tools, gaming, video and music, and so forth. Time dependent parameters that describe various aspects of femto cell access conditions are described in more detail below.

In general, systems and methods are provided to control access to a femto cell communication service through access control lists or white lists 230. Such white lists 230 can be configured via a networked interface (shown and described below) which facilitates access to the femto cell 210. In one aspect, time-dependent parameters are configured via the interface to enable a certain class of users to have access during designated periods or time intervals. For example, a home cell may have a white list configured to allow a maintenance user to have access during a specified time period when the user is at the home working to solve a problem. In a business application, employees may be enabled to access a cell during their normal working hours or for other specified periods of time. Access can also be changed for differing levels of security in view of the particular time that has been configured. Access can be dynamically monitored and changed over time based upon determined patterns of usage as will be described in more detail below with respect to FIGS. 5 and 6. Typical time-dependent parameters include time of day, calendar periods, user id's, event descriptors, access type, modality employed, or application type. Other parameters can include designated constraints that may apply for a given access.

Figure 3:
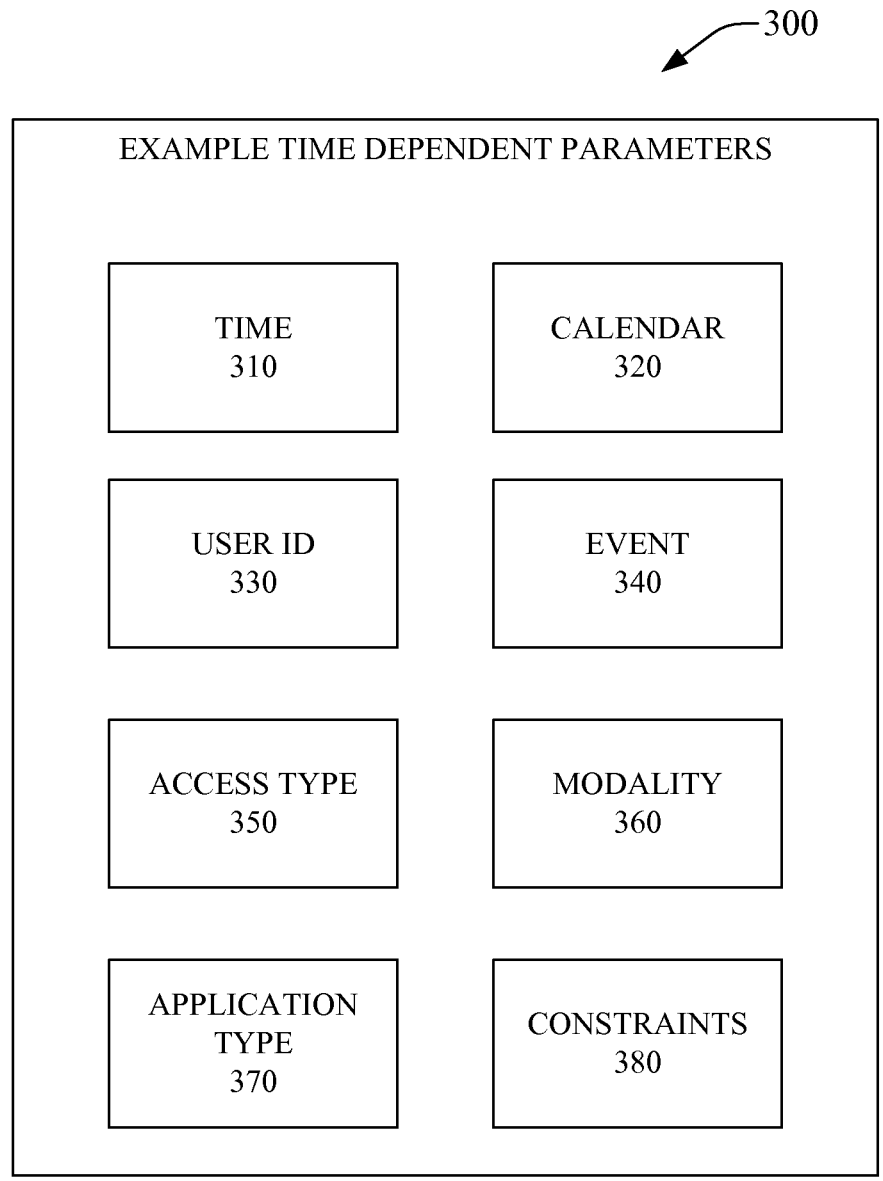
FIG. 3 is a diagram of exemplary time-dependent parameters for femto cell access.

FIG. 3 is a diagram of exemplary time-dependent parameters 300 for controlling femto cell access. At 310, one or more time parameters can be specified. These include explicit time designations such as 9:00 am, or 2:00 Pacific Standard time. These can include periods of time such as from 9:00 Am to 2:00 pm. These can also include implicit designations of time. For example, time access is granted for one hour if another user or device was previously granted access. This could include designating certain other activities or events as triggering conditions for the implicit time period. This can also include relative statements of time (e.g., access is granted for 1 hour after two days from previous access). At 320, calendar periods can be specified. These can include standard calendar interfaces that are provided that enable users to designate one or more periods of a calendar in which access is granted or denied. At 330, a user id can be specified that enables a particular user for a specified time or period. This can include enabling electronic id's that can be scanned from a given user that allow other time parameters to be applied for access to the respective femto cell.

Proceeding to 340, event types can be specified. These can include implicit designations that imply a period of time that if an event occurs that a particular user or device is enabled. For example, emergency events, routine events, maintenance events, and so forth. At 350, access types can be specified that further condition the application or time or periods to control access to the femto cell. These can include designations such as temporary access, permanent access, one time access, or access for a pre-determined or configured number of times. At 360, a type of interface modality can be specified that again can imply a particular time of access. For example, voice access is only granted during these times whereas e-mail access is granted during other times. Modalities can apply to any type of communications form including text, voice, or other communications codes.

At 370, application access can be specified. This can include enabling or disabling particular types of applications for predetermined periods as specified at 310 or 320 or limiting access to particular times based upon the application. For example, limiting gaming applications to non-working hours. Substantially any type of application can be specified including news, billing, metrics, business, and so forth. At 380, one or more constraints can be specified. These include rules or policies that define when access can be terminated in view of designated time periods. For instance, if a number of retries occurs before a given event has occurred or a number of password authentications has been exceed. Automatic logout procedures can also be specified if activity to the femto cell is not detected within a specified time.

Figure 4:
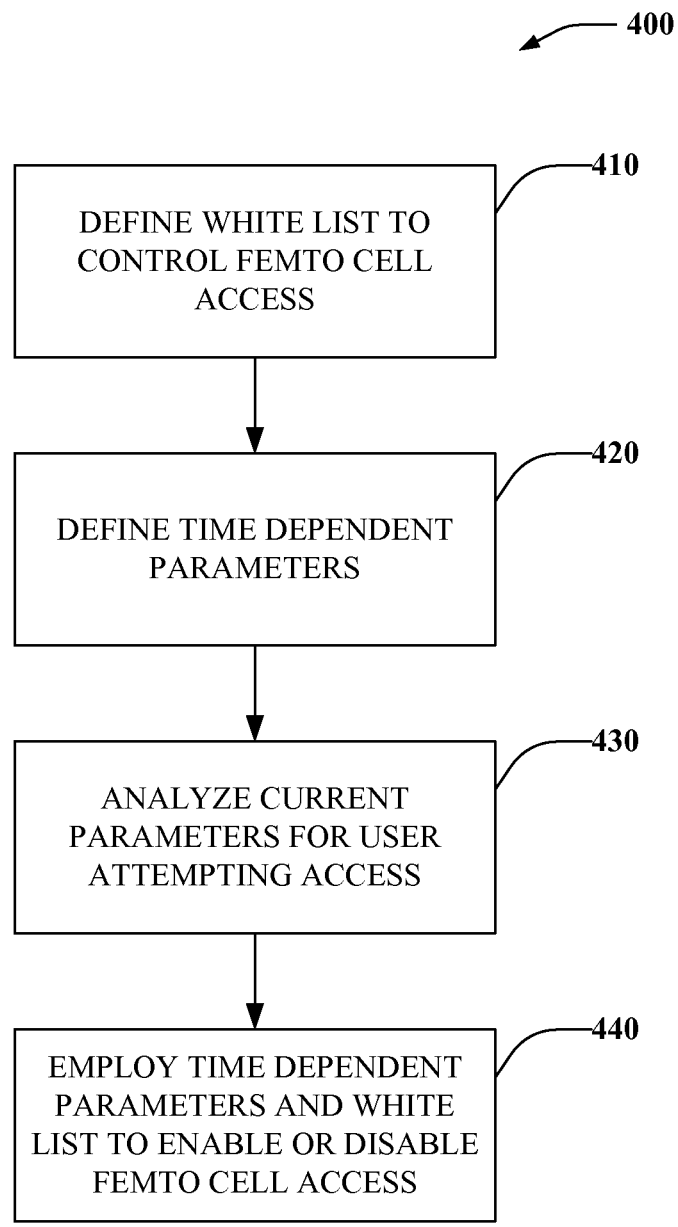
FIG. 4 is a flow diagram illustrating a method that employs time-dependent parameters to control access to a femto cell.

FIG. 4 is a flow diagram illustrating a method 400 that employs time-dependent parameters to control access to a femto cell. Proceeding to 410, a white list (also referred to as an access control list) is defined for a designated femto cell. The white list specifies conditions ion which users and/or devices are granted access to the respective femto cell. At 420, one or more time dependent parameters are defined. As noted previously, these can include explicit designations of time, implicit designations, and/or relative designations where time is specified in view of or in relation to some other specified time or period. Some example parameters include a time parameter, a calendar parameter, a user or device identification parameter, an event parameter, an access type parameter, a modality parameter, an application type parameter, and a constraint parameter. At 440, the time dependent parameters and the white list are employed to enable or disable access to the femto cell or cells. This can include real time monitoring of the parameters and disabling access as conditions change over time. This can also include analyzing an initial set of parameters, determining whether or not a user or device meets said parameters then granting access over the specified conditions defined by the respective parameters.

Figure 5:
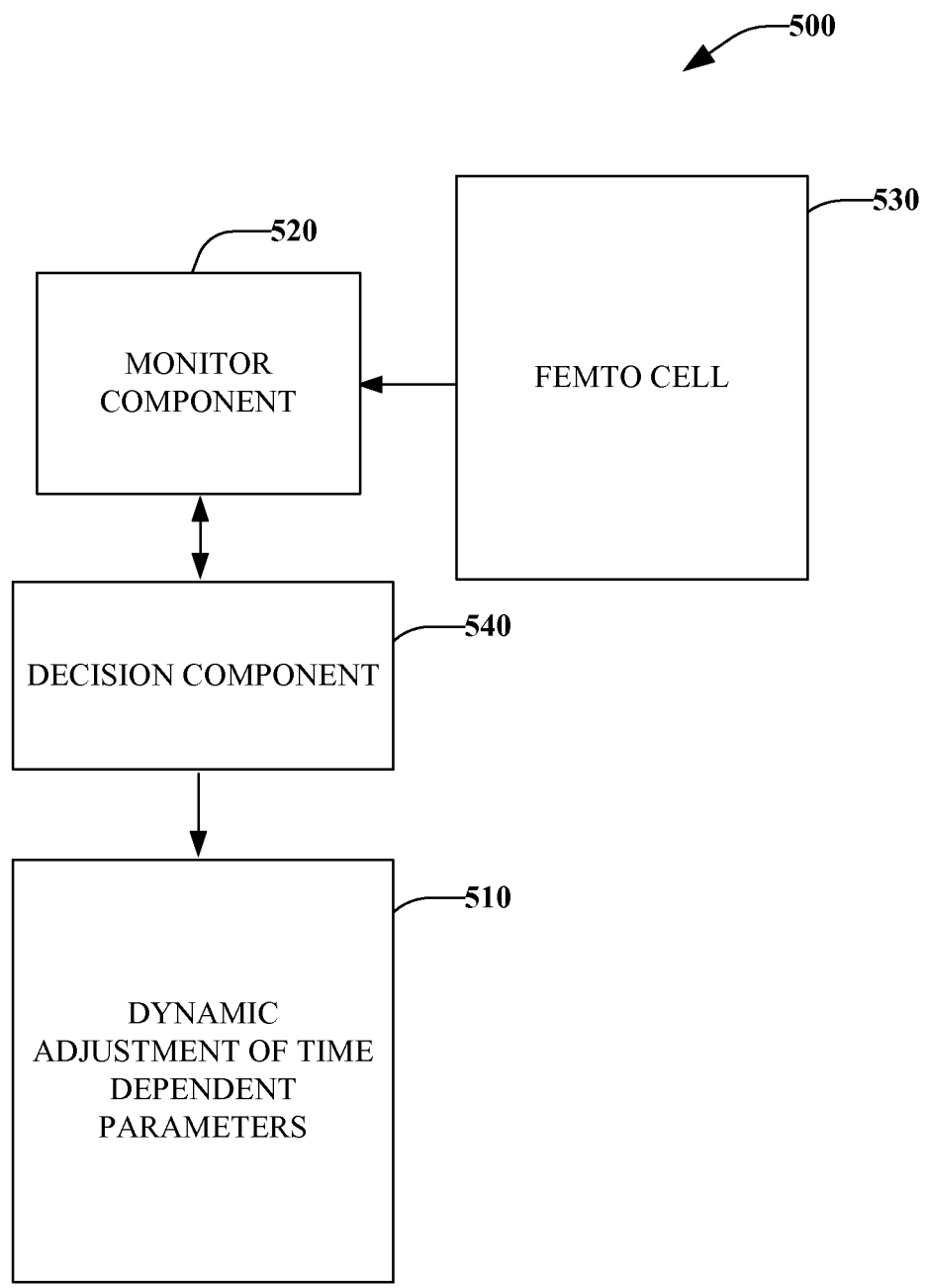
FIG. 5 is a block diagram illustrating a system that dynamically monitors and adjusts time-dependent parameters for femto cell access.

FIG. 5 is a block diagram illustrating a system 500 that dynamically monitors and adjusts time-dependent parameters for femto cell access. The system 500 is employed to be adaptive over time, where time dependent parameters 510 can be dynamically adjusted based upon observed system usage. A monitor component 520 monitors one or more aspects of a femto cell 530. The femto cell 530 can include access nodes that enable or disable access to one or more other nodes of the femto cell based upon one or more of the parameters 510. As shown, a decision component 540 receives data from the monitor component 520 and employs the data to determine whether or not one or more of the time dependent parameters 510 described above should be changed in view of various rules, policies, or other determinations such as intelligent classifiers that statistically determine baseline values for the parameters 510.

In one aspect, the decision component 540 may be set up as predetermined thresholds that allow given users or classes of users particular access to the femto cell 530 on a time dependent basis. For example, a threshold may be set up that one user is granted access between 9:00 and 12:00 each morning. Over time, the monitor component 520 may detect that the usage is always between 10:00 and 11:00 on three separate days, where usage is not attempted (or rarely attempted) otherwise. Based upon such detection, the decision component 540 could dynamically adjust the time and date parameters to the detected times and days that have been previously monitored. In other cases, it may be determined that a particular user needs more time, thus other periods and parameters for usage can be increased. Particular rules or policies can be pre-configured to determine how often or when particular parameters are adjusted. For instance, some users may be declared to never have their parameters adjusted whereas other users or classes may have parameters adjusted based upon observed usage over time. In addition to monitoring data against predetermined thresholds, statistical analysis may be applied where parameters are adjusted to some predetermined norm. For example, parameters may be adjusted to an average usage pattern, a peak usage pattern, an event pattern, a calendar period, and so forth.

In a more elaborate aspect, the decision component 540 may include intelligent aspects such as classifiers that analyze data from the monitor component 520 and adjust the parameters 510 based on observed or detected patterns of usage. This can include an inference component (not shown) that further enhances automated aspects utilizing, in part, inference based schemes to facilitate inferring time dependent access parameters 510. The classifiers can be implemented via any suitable machine learning based technique or statistical-based techniques or probabilistic-based techniques or fuzzy logic techniques. Specifically, these components can implement models based upon learning processes (e.g., confidence, inference). For example, a parameter adjustment model can be generated via an automatic classifier system. In another aspect, artificial intelligence can be applied as an optimization component. A typical optimizer can automatically run a model multiple times, for each run evaluating a unique combination of parameter values for a specified set of parameters, with the goal of finding the set of values that maximizes (or minimizes) some objective function—for instance increasing or decreasing time or calendar thresholds for enabling or disabling access to the femto cell 530.

A support vector machine (SVM) is an example of a classifier that can be employed. The SVM operates by finding a hypersurface in the space of possible inputs, which hypersurface attempts to split the triggering criteria from the non-triggering events. Intuitively, this makes the classification correct for testing data that is near, but not identical to training data (e.g., data from previous usage patterns or data from typical usage patterns of a group). Other directed and undirected model classification approaches include, e.g., naïve Bayes, Bayesian networks, decision trees, and probabilistic classification models providing different patterns of independence can be employed. Classification as used herein also is inclusive of statistical regression that is utilized to develop models of usage, access, or denial.

Classifiers can be explicitly trained (e.g., via a generic training data) as well as implicitly trained (e.g., via observing user behavior, receiving extrinsic information). For example, SVM's can be configured via a learning or training phase within a classifier constructor. In other words, the use of expert systems, fuzzy logic, support vector machines, greedy search algorithms, rule-based systems, Bayesian models (e.g., Bayesian networks), neural networks, other non-linear training techniques, data fusion, utility-based analytical systems, systems employing Bayesian models, etc. are contemplated and are intended to fall within the scope of the hereto appended claims. Other implementations of AI could include alternative aspects whereby based upon a learned or predicted user intention, the system can generate further parameter adjustments.

Figure 6:
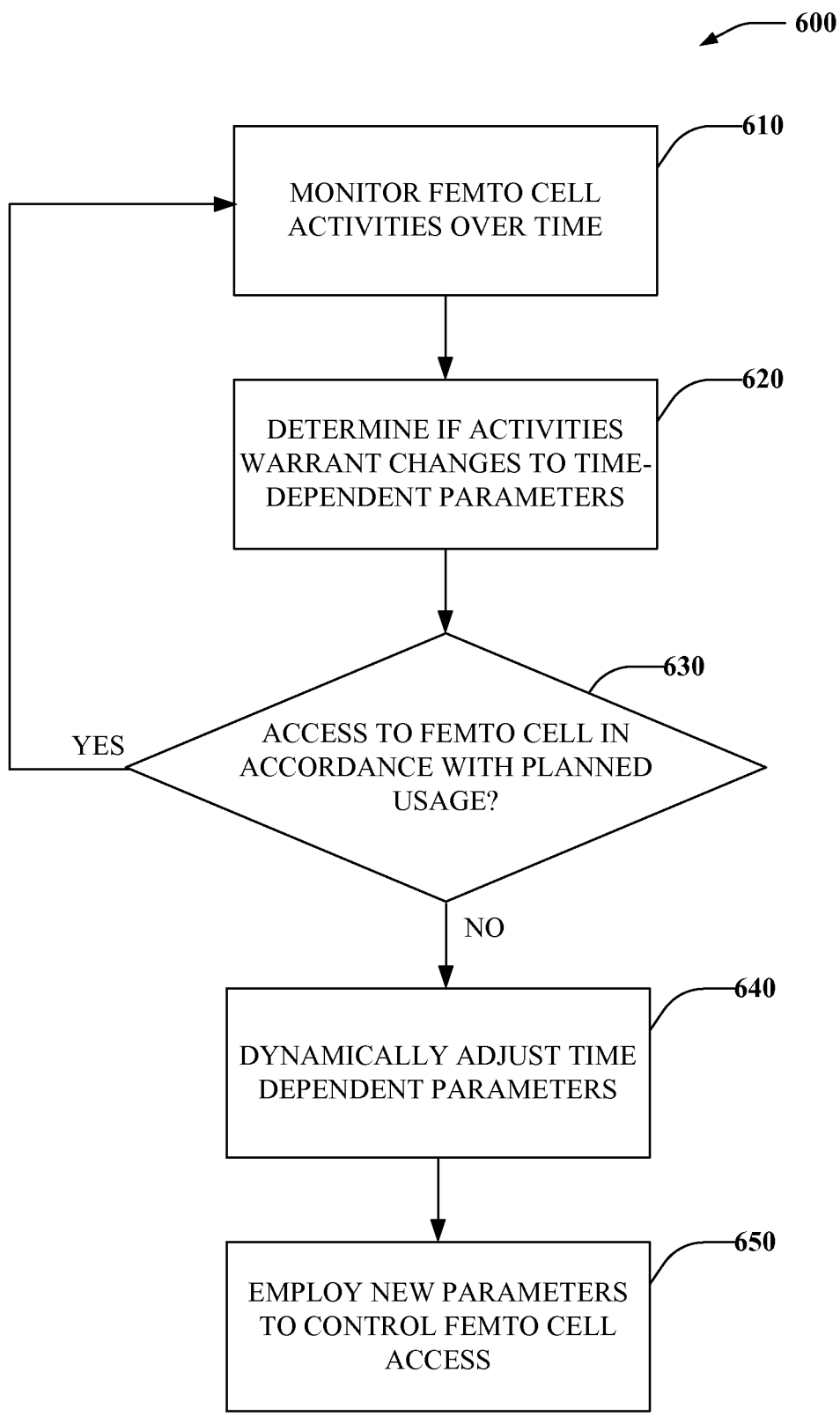
FIG. 6 is a flow diagram illustrating a method that dynamically adjusts time-dependent parameters for femto cell access.

FIG. 6 is a flow diagram illustrating a method 600 that dynamically adjusts time-dependent parameters for femto cell access. The method 600 describes automated processes for monitoring femto cell activity over time and dynamically adjusting time-dependent access parameters over time in view of such monitoring. Predetermined thresholds and rules or policies can be set up to determine whether or not such changes are warranted or what conditions might be suitable that lead to a dynamic adjustment.

Proceeding to 610, femto cell activity is monitored over time. This can include who is accessing a particular cell, what times are being accessed, how long the access occurs, during which calendar periods access is occurring, monitoring what type of access (e.g., read data only, read and write data and so forth), the type of applications that are being employed, and so forth. Based upon the monitoring at 610, data is analyzed at 620 to determine if prior usage activities warrant changes to the time dependent parameters described above. For example, one user may be granted access a specified periods of a week and it is found that only one period is ever utilized for access. In this case, usage periods can be adjusted to the determined period of activity. In another example, it may be determined that a trusted user is frequently getting time-out of the system. The user could send a message requesting more time. Based upon the status of a given user, the method could automatically grant more time. Other users who are as trusted can be denied being granted more time. In yet another example, it may be determined that a user only requests access with a particular type of device. Based on such usage, modality parameters can be adjusted to allow access to the detected device while limiting access to non-used devices. As can be appreciated, user can be given classifications where some users may not have there parameters adjusted and others may be highly-tuned to detected usage patterns.

Proceeding to 630, a decision is made as to whether or access to a femto cell is in accordance with planned usage. This may include comparing usage patterns to predetermined thresholds such as comparing whether or not a user typically access the femto cell during pre-defined periods. In other cases, the thresholds may be automatically set by monitoring initial usage periods to automatically determine usage periods. For example, a user may be told that during a given calendar period, usage is unrestricted. During that period of activity, threshold times for usage will be monitored, detected and set. If access to the femto cell is according to planned usage patterns or automatically detected patterns at 630, the process proceeds back to 610 and continues to monitor femto cell activity. If usage pattern is different than expected patterns as defined by the initial access parameters or initially detected usage patterns, the process proceeds to 640 and dynamically adjusts time dependent parameters. As noted previously, such parameters can be tied to user classifications, time periods, calendar periods, events, access types, modalities, applications types, or other constraints on usage. After the parameters have been adjusted at 640, the new parameters are them employed to regulate further access to the femto cell (or cells). After adjustment, the process can proceed back to 610 to further monitor femto cell activities.

Figure 7:
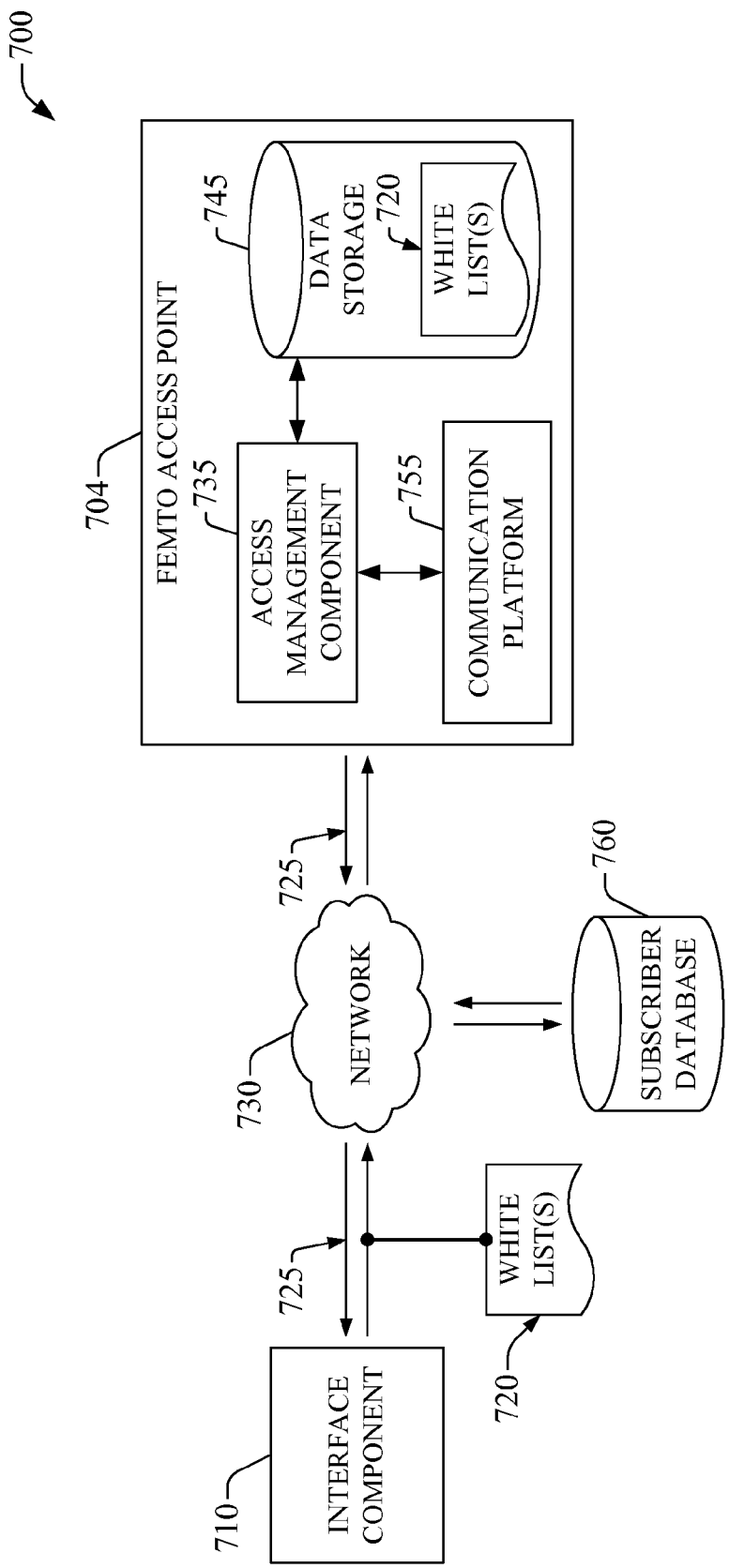
FIG. 7 is a block diagram of an example system that facilitates selection of subscribers to access coverage from a femto cell in accordance with aspects disclosed herein.

FIG. 7 is a block diagram of an example system 700 that facilitates selection of subscribers to access coverage from a femto cell; selection can enable or disable coverage for specific subscriber(s) or subscriber station(s). Means provided by example system 200 to authorize or revoke access to specific subscribers, or subscriber station(s), comprise what is herein termed as a "White List"—an instrument for management of access to femto cell coverage.

In example system 700, a femto access point 704 is provided where an interface component 710 facilitates configuration, or set up, of a list (e.g., white list 220) of wireless mobile station numbers approved for coverage through the femto access point 704. It is to be noted that substantially any identification token(s), label(s), or code(s) that indentify a subscriber station can be employed. Interface 710 is networked (e.g., via a WAN, LAN, or backhaul pipe) with femto AP 704 and convey white list 720 over network link(s) 725. In an aspect, interface component 710 can be a web-based, online graphic user interface (GUI); however, other networked interfaces that facilitates to enter, or configure, a white list are possible; for instance, voice or sound commanded interface(s), touch commanded interface(s), biometric commanded interfaces(s), and the like. A communication platform 755 facilitates reception of the white list(s) 720 and conveys white list(s) 720 to an access management component 735 that can exploit the white list(s) 720 to manage access to coverage provided by femto AP 704. White list(s) 720 can be stored in the data storage 745 in the femto AP 704; even though white list(s) 720 can be stored in disparate network components like network component administered by a service operator. In addition, interface component 710 can access a subscriber database through network 730, in order to extract identification numbers, codes, tokens, or labels for subscribers/subscriber stations that can be entered in a white list.

In an illustrative, not-limiting aspect of the innovation, white list(s) 720 (or any set of numbers, codes or tokens thereon, that comprise a set of mobile phones approved for coverage by femto AP 704 can be portable through accounts or billing groups associated with a set of subscribers to a service operator that administers femto AP 704, or a macro network. As an illustration, white list(s) 720 can support up to N fields (N a positive integer; e.g., N=50) for unique mobile phone numbers (e.g., MSIDSNs), or any suitable identifying codes or tokens. The number N of fields can be determined, or configured, by a service operator based at least in part on technical aspects (like network resources, quality of service consideration, macro area of coverage (e.g., MSA/RSA), and so on) and commercial aspects (such as promotional considerations, mitigation of customer attrition, gains in market share, etc.) aspects of provision of coverage. As an example, N can be subscriber dependent or femto AP dependent.

In contras to management of access authorization via femto access point 704, it should be appreciated that configuration of white list(s) 720 (registration authorization for femto coverage) through a network mechanisms (e.g., interface component 710) provides at least the following advantages. It is to be noted that the following advantages are illustrative and not limiting, as other advantages associated with white list(s) 720 are possible and are intended to lay within the scope of the innovation(s) described in the subject specification. (1) Access through an networked interface (online or otherwise) reduces provisioning lead time and provides a means for customers to update and personalize femto AP autonomously (e.g., free of interaction with technical support entities) at substantially any time. (2) Security against devices attempting to hack into the femto AP when networked with it, and support of extensible sharing/networking of the authorization scheme. (3) Networked interface (online or otherwise) provides a superior, rich customer experience substantially free of requirement(s) to understand/interpret femto AP programming interface or configuration nomenclature. (4) End user(s) can manage (e.g., remove select covered numbers, or add additional numbers for coverage up to an allotted amount for white list(s) associated with the user. (5) Capacity to determined quality of service, grade of service, or service experience, for specific authorized subscribers. (6) Capacity to check for valid wireless device numbers, codes or tokens (e.g., MSISDNs); subscriber's active numbers, codes or tokens; and numbers, codes or tokens on service accounts in good standing; such capacity can be provided through networked access to a subscriber database 760.

White list(s) 720 facilitates management of access to coverage by a femto AP (e.g., femto AP 704). Various illustrative aspects of innovation based at least in part on a white list concept are discussed next. It is to be noted, notwithstanding, that variations and extensions of such illustrative aspects are possible and are within the scope of the subject innovation.

Figure 8:
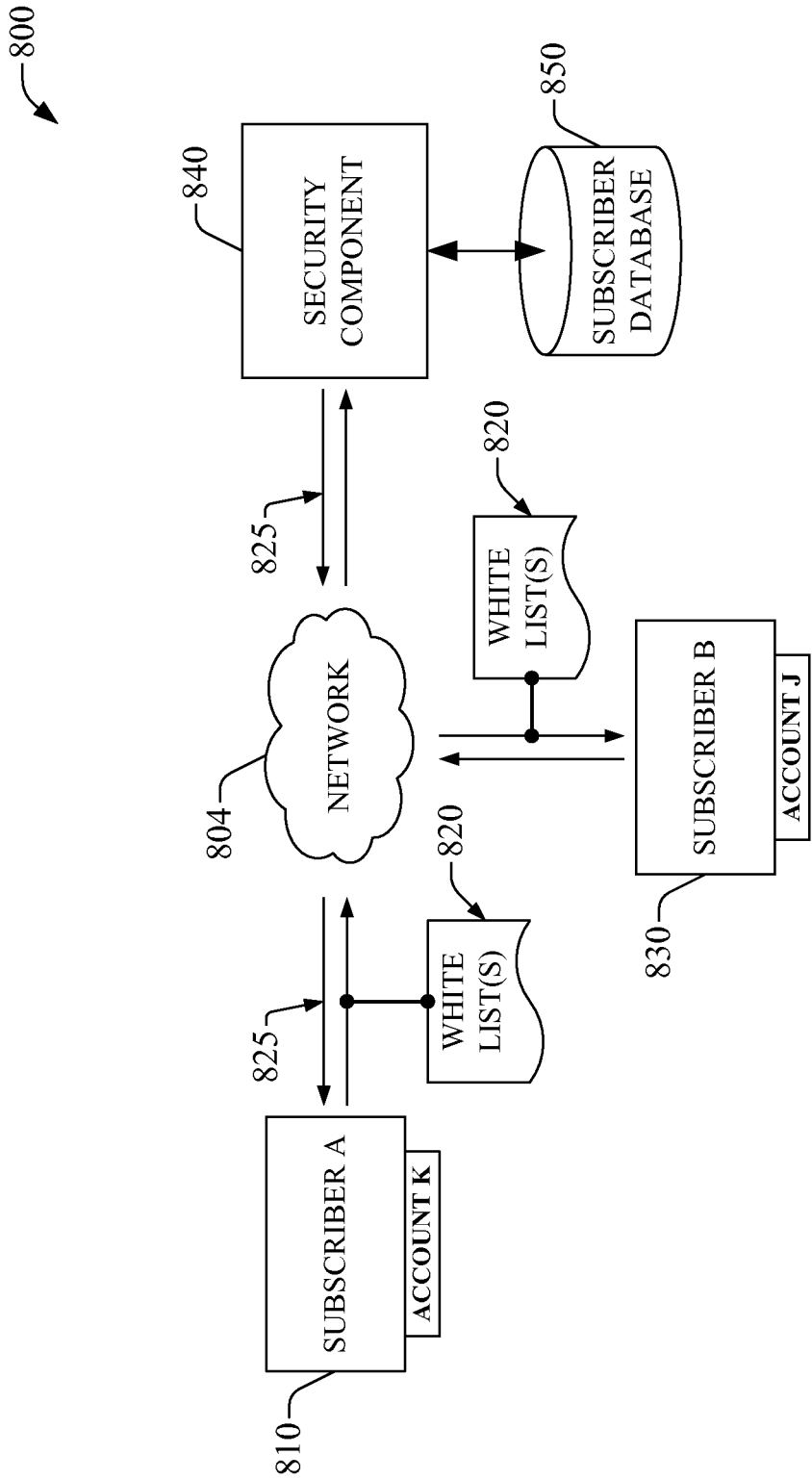
FIG. 8 is a block diagram of an example system to share access control list(s), or white list(s), in accordance with aspects described herein.

FIG. 8 is a block diagram of an example system 800 and network 804 to share access control list(s), or white list(s) 820, among subscribers of a wireless network service in order to provide straightforward access configuration to, and activation of, a femto cell (e.g., femto AP 130) among femto cell subscribers. Subscribers can belong to disparate or same service accounts with either a macro service provider or femto provide, or both. For example, subscribers that share white list(s) can pertain to a group or family associated with a single service account. In example system 800, subscriber A 810 who belongs to account K conveys white list(s) 820 over network 804, via a wired or wireless link 825, to subscriber B 830 who belongs to account J. Subscriber A 810 can hide or eliminate specific subscriber station numbers from white list(s) 820 he/she/it grants to other subscribers. It should be appreciated that the granting of subscriber station numbers, codes or tokens can substantially reduce the amount of time to configure, or set up a white list, as opposed to manually re-entering multiple (e.g., up to 50 numbers, codes or tokens) across multiple femto cells.

A security component 840, or authorization layer, can ensure that unauthorized mobile subscriber numbers, codes or tokens, are not provided when not approved by end users. Such approval can be determined via a privacy policy associated with the end user, or subscriber, which can be stored in a subscriber database 850; the privacy policy can be configured/updated through various means like web-based interfaces, call center, text-message center, and so on. Security component 840 ensure privacy integrity when white list(s) 820 are shared among subscribers of different accounts (e.g., J≠K). In an illustrative aspect, security component 840 can solicit subscribers outside a "white-list share" originating account to grant the authority for their subscriber station identifier number, code or token to be shared through white list(s). To the latter end, security component 840 can resort to various mechanisms that include, but are not limited to including, a short message service (SMS) communication, a multimedia message service (MMS) communication, email, voice mail, web pop up, and so on. Alternatively, or in addition, security component 840 can mitigate security mechanism(s) complexity through validation via subscriber account information (e.g., stored in subscriber database 850) in order to grant automatic access to white list(s) within groups or families underneath a single service account, without additional security verification.

Figure 9:
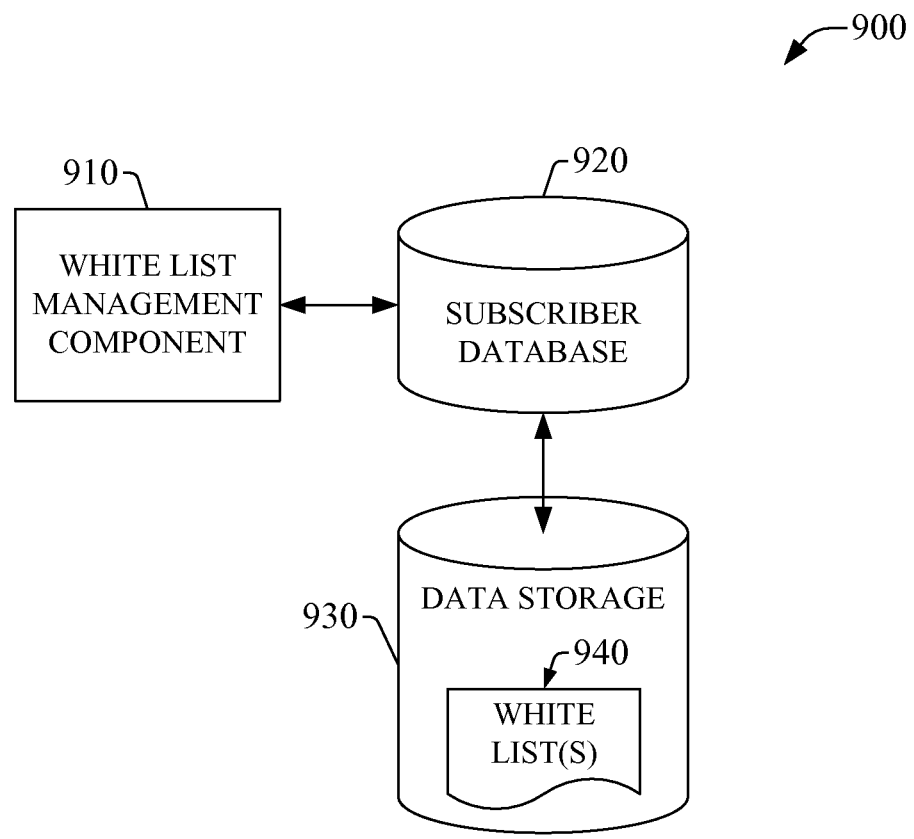
FIG. 9 is a block diagram of an example system that manages access control lists, or white lists, in accordance with aspects described herein.

FIG. 9 is a block diagram of an example system 900 that manages access control lists, or white lists. White list management component 910 accesses a subscriber database 920 which can be maintained by a service operator for femto and macro cells, and a data storage 930 that retains a set of white lists 940 associated with serviced subscribers, to associate white-listed subscribers across disparate access control lists. Such association can lead to genesis of white-lists trees. In an aspect, white list management component can implement mechanisms to mitigate exponential data growth and efficient storage of white-list trees like data-compression (e.g., wavelet, efficient tree representation, and so on), distributed data warehouses, and so forth. In another aspect, white list management component can deploy a white-list tree in accordance to the following illustrative, non-limiting scenario. (i) User 1 adds User 2 to his/her white list. (ii) User 2 adds User 3 to his/her white list. (iii) User 1 and User 3 can be associated through white lists. (iv) User 1 and User 3 can match User 4 extant on each other's white lists. (v) User 1 and User 3 can associate User 5 that is on User 4's white list. White list management component 910 effects associations and manages generated white-list tree(s). It should be appreciated that substantially any association, hierarchical or non-hierarchical, or deployment of white lists can be implemented by white list management component 910 through information stored in subscriber database 920 and data storage 930.

An illustrative, non-limiting, advantage of structured, hierarchical generation of white lists to subscribers (e.g., subscriber A 310) is that more subscribers can have access femto cells to gain coverage enhancement, or have access to added value through unlimited usage on any femto cell or unique services available via a set of femto cells.

In addition, example system 900 can track subscriber station identifier numbers (e.g., MSISDNs), codes or tokens, associated with white list(s) on record with a femto service provider. White list management component 910 can validate white list(s) 940, stored in data storage 930, against current accounts and associated subscriber station identifier numbers (e.g., MSISDNs), codes, or tokens, for a service provider. In particular, when a subscriber, or end user, cancels an account with service provider, white list(s) 940 can be updated according to information retrieved from subscriber database 920, or substantially any other database available to a service provider that contains information on service subscribers. In addition, when an end user changes their mobile or subscriber station number, code or token, (e.g., after relocation to a new area code, or the like) substantially all white list(s) 940 that the mobile or subscriber station number, code or token is associated with can automatically be updated by white list management component 910.

An illustrative advantage of such automatic update of white list(s) 940 is ease of use for end users to maintain current white list(s) 940 without a need to keep track of each subscriber station number, code or token associated with the white list(s) 940. In addition, updated white list(s) 940 maintains the value proposition of the femto cells for end users and service operator by a seamless move of traffic off of the macro network (e.g., a WAN) to femto network(s).

Figure 10:
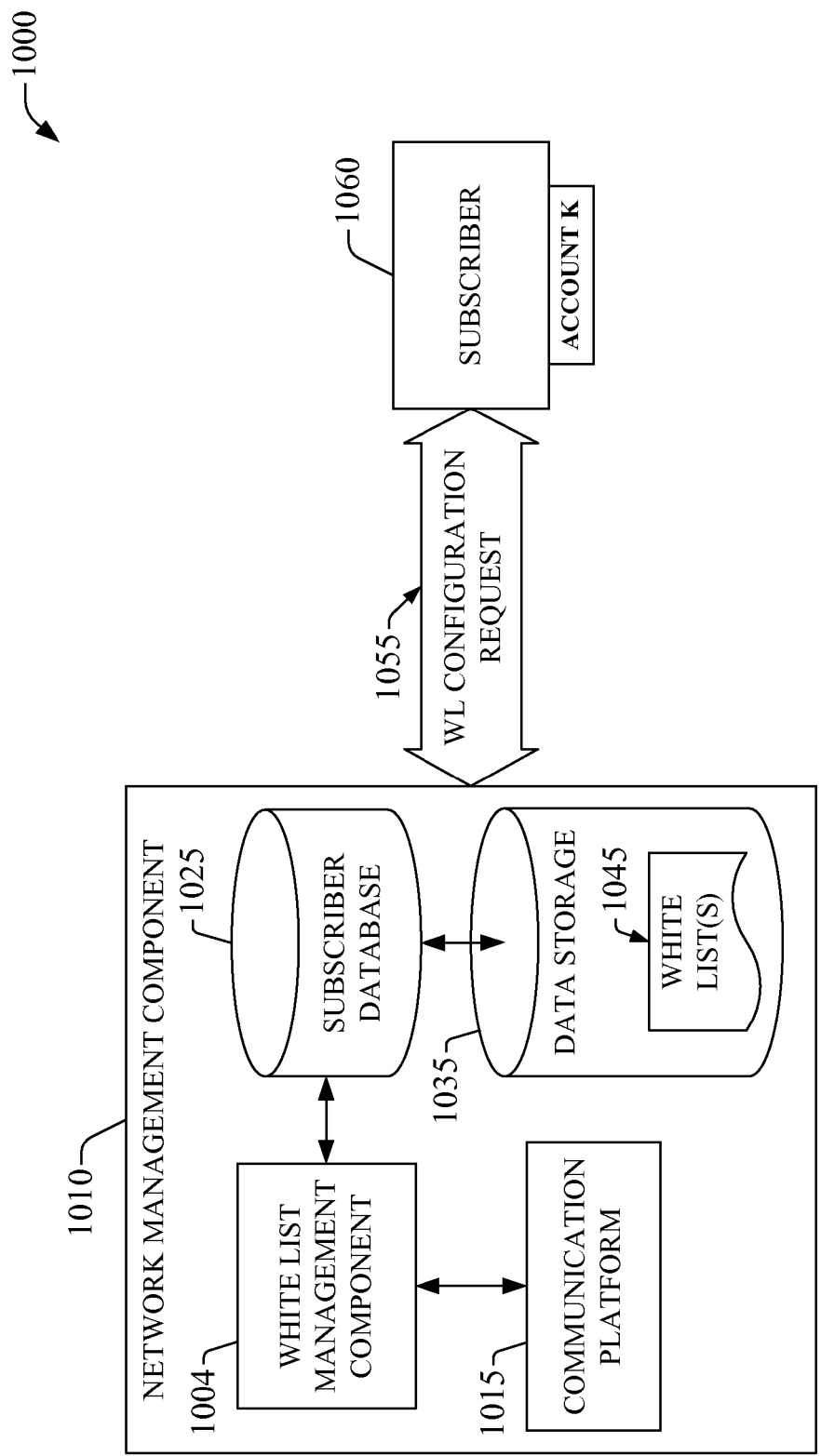
FIG. 10 is a block diagram of an example system that facilitates addition of subscriber(s)/subscriber station(s) to one or more white lists in accordance with aspects described in the subject specification.

FIG. 10 is a block diagram of an example system 1000 that facilitates addition of subscriber(s)/subscriber station(s) to one or more white lists. In example system 1000, a network management component 1010 includes a white list management component 1004 which is coupled to a subscriber database 1025, a data storage 1035 and a communication platform 1015. The white list management component 410 can datamine subscriber database 1025 and white list(s) 1045, which resides in data storage 1035, to drive addition of new subscribers to a white list to request reciprocal adding. In an aspect, when a subscriber 1060 in account K is identified for reciprocal addition at a time the subscriber 1060 configures his/her femto AP, a white list (WL) configuration request 1055 is conveyed (e.g., via a wired or wireless link through communication platform 1015) to the subscriber. Such configuration request indicates that a disparate subscriber has subscriber 1060 white-listed and prompts subscriber 1060 to include in his/her white list the disparate subscriber. An illustrative scenario is the following: User 1 adds User 2 to his/her white list. When User 2 configures/activates his/her femto cell, a setup process (implemented, for example, through a web-based online GUI) will prompt User 2 to add User 1. It is to be noted that white list management component 410 can exploit information in subscriber database 1025 and data storage 1035 to inform User 2 of substantially all subscriber station numbers, codes or tokens that he/she can add automatically on a reciprocity basis; namely, User 2 can be prompted to add in white list(s) those subscribers that have previously added him/her to their with list(s). White list configuration request 1055 can be effected through various interfaces like an online GUI, a real time prompt/alert delivered via SMS, MMS, email, instant message, and so forth.

Figure 11:
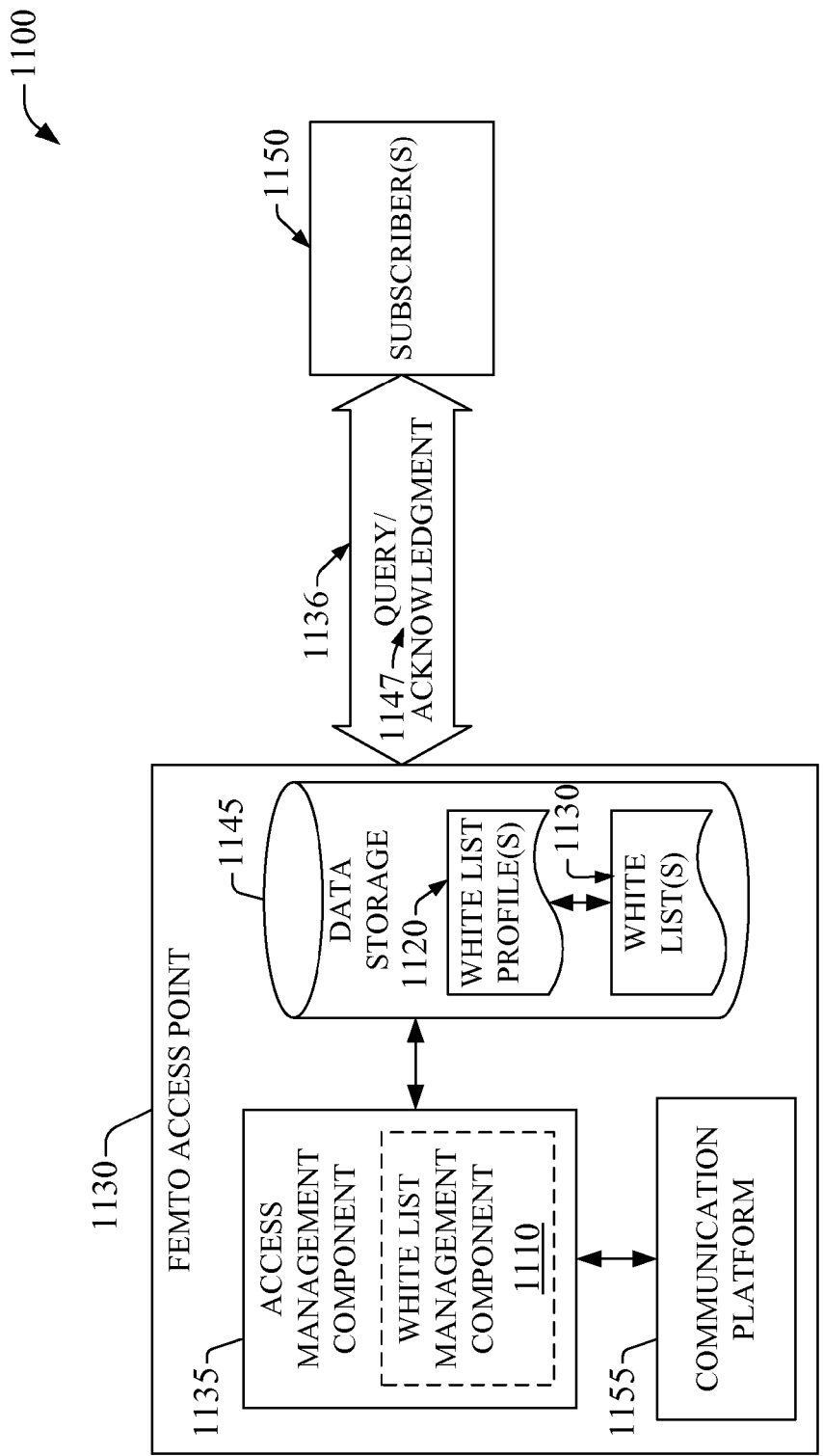
FIG. 11 is a block diagram of an example system that manages a defined logic of how content(s) (e.g., MSISDNs) in access control list(s), or white list(s) is maintained on a white list database in accordance with aspects described herein.

FIG. 11 is a block diagram of an example system that manages a defined logic of how content(s) (e.g., MSISDNs) in access control list(s), or white list(s) is maintained on a white list database. Access management component 1135, which can comprise a white list management component 1110, can develop white list profile(s) 1120 that applies logic and parameters that control, or manage, content in white list(s) 1130 such as subscriber station numbers (e.g., MSISDNs), codes or tokens. White list profile(s) 1120 and white list(s) 1130 can be stored in data storage 1145; it should be appreciated that while data storage 1145 is illustrated to reside within femto access point 1130, such storage can reside in a network management component (e.g., component 510).

In an aspect, white list profile parameters that control utilization logic of white list(s) content include, without being limited to including: (i) temporary access, e.g., full access for a specific time interval such as days or hours; (ii) access only within a window of time in a day (voice and data allowed from 9:00 a-6:00 p, or voice allowed after 9:00 p which can facilitate billing schemes already established by an operator/service provider); and (iii) access to specific applications such as scheduler, calendar(s), news streaming, authoring tools, gaming, video and music, etc.

In another aspect, logic within white list profile(s) can implement parameters to determine how long access to femto coverage is granted. For instance, when a timer associated with temporary access expires, a query 1147 can be conveyed (e.g., through a wired or wireless link 1136) to either a subscriber that operates a device associated with the managed MSISDN in order to request renewed access, or to a subscriber that operates femto access point 1130. The message request, e.g., query 1147, can ask the owner if an extension should be granted or not. When a request is not granted by a subscriber that operates femto AP 1130 or there is no reply, e.g., acknowledgement 1147, from the subscriber, access to femto coverage expires and the MSISDN (or substantially any identifier code or token) is deleted from a corresponding white list(s) within data storage 1145. Conversely, a positive response, e.g., acknowledgement 1147, can allow access to continue based on either parameters extant in white list profile(s) or newly defined parameters. It is to be noted that query 1147 can be conveyed via an online GUI, an email message, a SMS message, MMS message, a voice mail, a web prompt, and the like.

Figure 12:
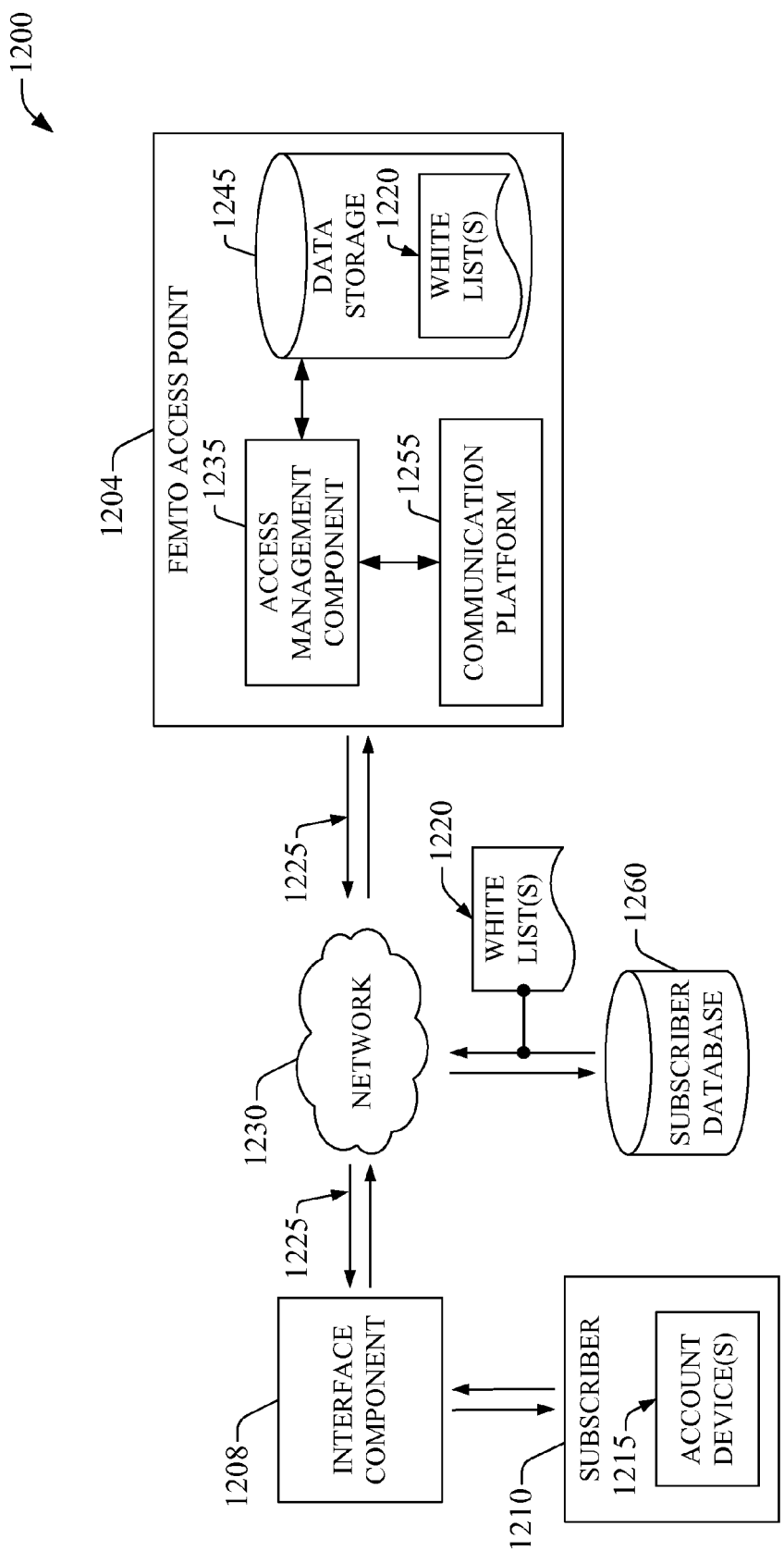
FIG. 12 is a block diagram of an example system that initializes access control list(s), or white list(s), to femto coverage with subscriber station identifier numbers, codes or tokens available on a service account in accordance with aspects disclosed herein.

FIG. 12 is a block diagram of an example system 1200 that initializes access control list(s), or white list(s), to femto coverage with available subscriber station identifier numbers, codes or tokens available on a service account. In example system 1200, a subscriber 1210 who utilizes device(s) 1215, can provision femto AP 1204 and associate the device(s) 1215 with a service account via a networked interface component 1208 (e.g., an online account management system) which can look up into substantially all subscriber station(s) identifier numbers (e.g., MSISDNs), codes or tokens associated with the service account, and automatically populates white list(s) 1220 with the extracted subscriber station(s) numbers, codes or tokens. Subscriber 1210, via interface component 1208, can remove or add subscriber station(s) numbers (e.g., MSIS-DNs), codes or tokens extant in a pre-populated white list(s) 1220; additional edits can be performed as well, based at least in part on the complexity of white list(s) 1220. In an aspect, to pre-set white list(s) 1220, networked interface component 1208 access information stored in subscriber database 1260 through network 1230 which can include information technology systems of a service provider. White list(s) 1220 is conveyed through network 1230 to femto access point 1204; a communication platform receives white list(s) 1220 and access management component 1235 stores the white list(s) 1220 in data storage 1245.

An illustrative advantages provided by example system 1200 are (a) reduced femto cell provisioning lead time, and (b) immediate utilization of a femto cell with mobile numbers that belong to a same service account, whether subscribers of such numbers subscribe to the femto cell or a feature application, or code, that delivers a femto cell service.

Figure 13:
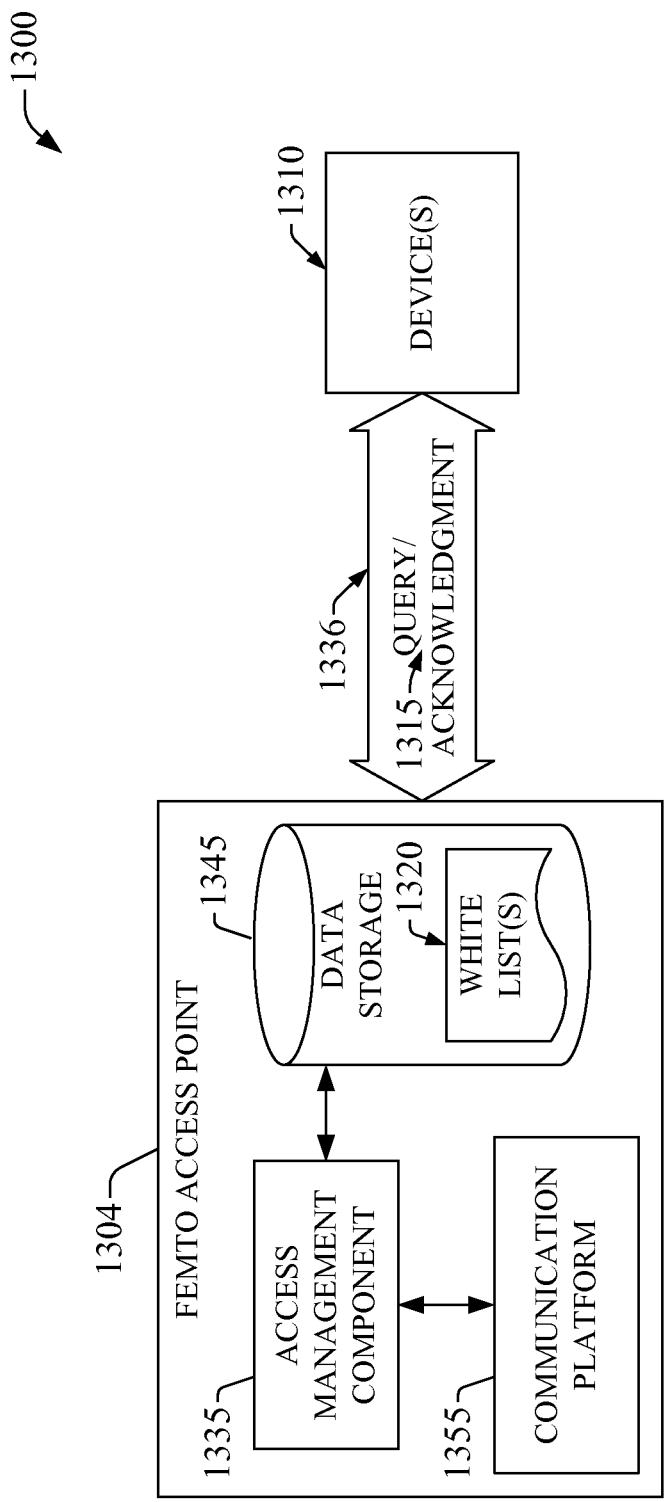
FIG. 13 is a block diagram of an example system 800 that facilitates addition of wireless, mobile devices on an ad hoc basis in accordance with aspects described herein.

FIG. 13 is a block diagram of an example system 1300 that facilitates addition of wireless, mobile devices on an ad hoc basis. In example system 800, device(s) 1310 can convey a request or query 1315 to access coverage of femto AP 1304. Such a request can be received by communication platform 1355, and access management component 1335 can be set up to allow or reject the request; allowance of rejection of a request can be based on various metrics, such as security, type of device, profile of subscriber that operated the device that requests access, and so on. Upon allowance of a request, access management component 1335 can query for available slots to be filled in white list(s) 1320 associated with accounts served by femto AP 1304, when space is available for a subscriber station identifier number (e.g., MSISDN), code or token, the query can further probe whether access is allowed on a permanent, or temporary basis (e.g., to reduce risk exposure to security problems). Characteristics of femto coverage allowance can be set or pre-set through access management component 1325. Subsequent to allowance and examination of information related to relevant white list(s) 1320, access management component 1335 updates white list(s) 1320, stored in data storage 1345, to reflect the approved request for femto coverage. It is to be noted that access and update of collected subscriber identifier numbers (e.g., MSISDN), codes or token, can also be effected through network-based white list database(s). It is to be noted that query 1315 can be conveyed via an online GUI, an email message, a SMS message, MMS message, a voice mail, a web prompt, USSD (or * and # codes), and the like.

An illustrative, non-limiting advantage of example system 1300 is that it provides an enhanced end user experience with a direct, clear mechanism and thus encourages use of the femto access point 1304, and avoids time spent on edition of white list(s) through a networked interface like an online interface which takes time for the end user to have access to the Internet, and to log on in a secured interface.

It should be appreciated that substantially any wireless device within coverage area of femto AP 1304 can request access without intervention by a subscriber that operates femto AP 1304, and who has previously entered a set of subscriber station numbers (e.g., MSISDNs), codes or tokens, via a networked interface (e.g., interface component 710). Alternatively, or in addition, a request for access can be prompted by a device utilized by a subscriber that operates the femto AP. Further a request for access can be effected by the femto AP, through an access management component like component 1325, for example. When a request is granted, a secure tunnel can be established from the device/client through the femto cell's IP connection or the default of the Radio Access Network if the IP connection is not available. Secure layers including utilizing the femto cell's VPN and/or USSD would ensure that the transaction is in fact secure. As a non-limiting example, a temporary visitor or employee (e.g., a babysitter) who is coming over to a location served by a femto access point (e.g., femto AP 1304) for a limited period of time, can be provided with coverage via the femto AP by a subscriber that operates the femto cell so the employee can perform, at least in part, his work activities (e.g., provide updates on behavior of children) through utilization of the femto access point. In case the subscriber fails to know identifier numbers, codes or tokens for devices the employee can utilize, and the subscriber is not interested to go through the process of requesting and entering the numbers, codes or tokens via a networked interface to allow coverage for the limited period of time the employee performs work, the employee (e.g., babysitter) can convey a request (e.g., query 1315) invention allows the baby sitter to request femto access directly from the employee's device when in range of the femto access point.

In view of the example systems described above, example methodologies that can be implemented in accordance with the disclosed subject matter can be better appreciated with reference to flowcharts described herein. For purposes of simplicity of explanation example methods are presented and described as a series of acts; however, it is to be understood and appreciated that the claimed subject matter is not limited by the order of acts, as some acts may occur in different orders and/or concurrently with other acts from that shown and described herein. For example, those skilled in the art will understand and appreciate that a methodology could alternatively be represented as a series of interrelated states or events, such as in a state diagram, or interaction diagram. Moreover, not all illustrated acts may be required to implement a methodology in accordance with the subject specification. Additionally, it should be further appreciated that the methodologies disclosed hereinafter and throughout this specification are capable of being stored on an article of manufacture to facilitate transporting and transferring such methodologies to computers for execution by a processor or for storage in a memory.

Figure 14:
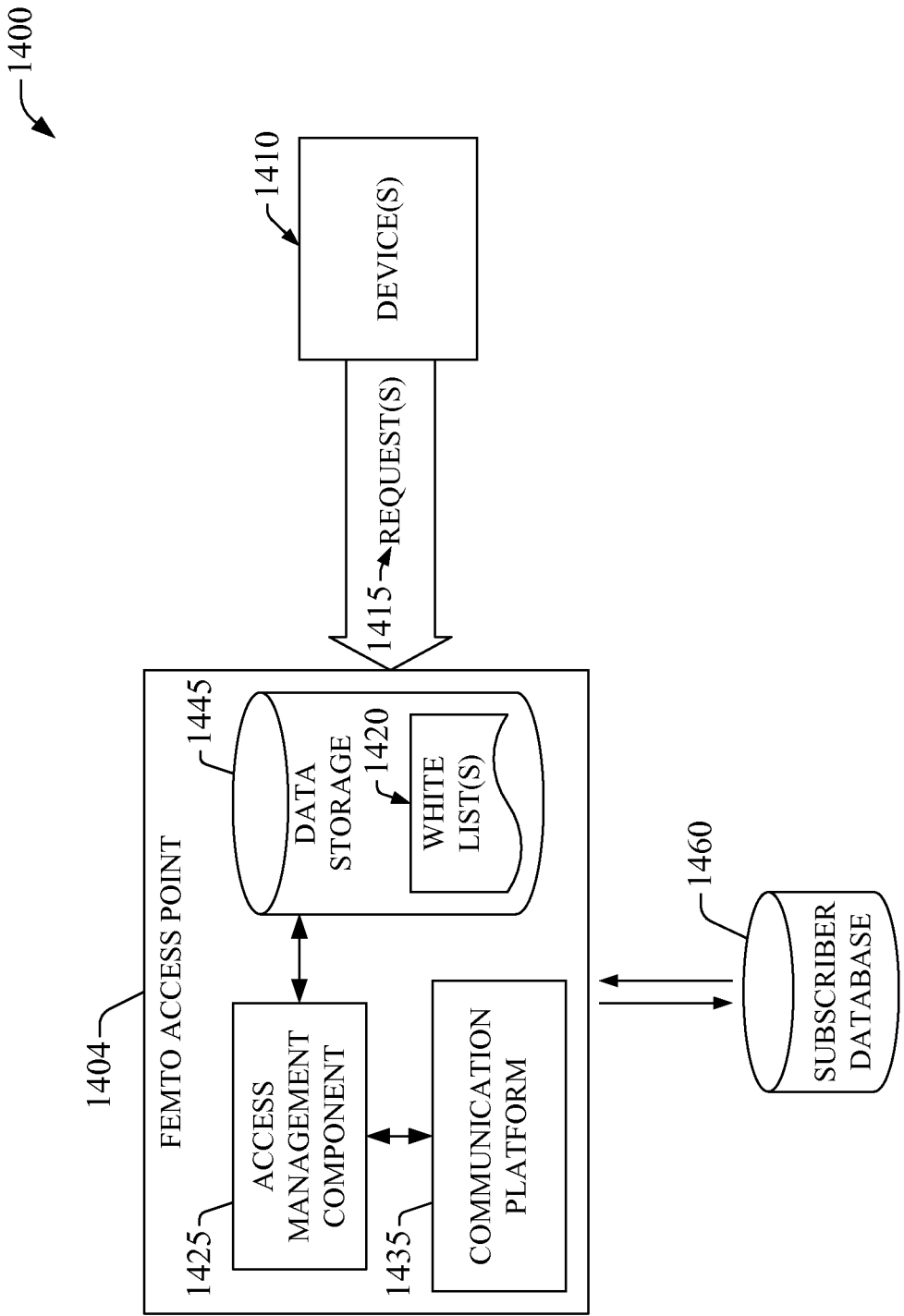
FIG. 14 is a block diagram of an example system that tracks subscriber station identifier numbers (e.g., MSISDNs), codes or tokens, associated with white list(s) on record with a femto service provider in accordance with aspects of the disclosed subject matter.

FIG. 14 is a block diagram of an example system 1400 that tracks subscriber station identifier numbers (e.g., MSISDNs, IMSIs), codes or tokens, associated with white list(s) on record with a femto service provider in accordance with aspects of the subject innovation. When a subscriber or end user, that operates mobile device(s) 1410 cancels an account or subscription with a service provider or changes identifier number, code, or token associated with mobile device(s) 1410, the subscriber can convey a request 1415 via mobile device(s) 1410 to remove the identifier number thereof from substantially all, or all, white list(s) 1420 on record in a subscriber database 1460 or substantially any other database available to a service provider that contains information on service subscribers. In an aspect, access management component 1425 can convey an indication to update white lists to a mobile wireless platform (e.g., a core network) in accordance to request(s) 1415. It is noted that local records of white list(s) 1420 are also updated; local update takes place in all femto APs that include white list(s) that comprise mobile device 1410 identifier number that is cancelled.

Additionally, or alternatively, when an end user changes his/her mobile or subscriber station number, code or token, (e.g., after relocation to a new area code, or the like), request(s) 1415 can be delivered to femto access point 1404 to automatically update substantially all, or all, white list(s) 1420 on record that include mobile device 1410 identifier number, code, or token. Access management component 1425 can deliver signaling to a mobile network platform to update white list(s) 1420 records in subscriber database 1460. It is noted that local records of white list(s) 1420 are also updated.

An illustrative advantage of such on-request automatic update of white list(s) 1420, and local white list(s) 1420, is ease of use for end users to maintain current white lists at the network level and local, e.g., femto AP 1404, level without a need to track each subscriber station number, code, or token associated with the white list(s) 1420. In addition, updated white list(s) 1420 and white list(s) 1420 maintain the value proposition of the femto cells for end users and service operator by a seamless move of traffic off of the macro network (e.g., a WAN) to femto network(s).

Figure 15:
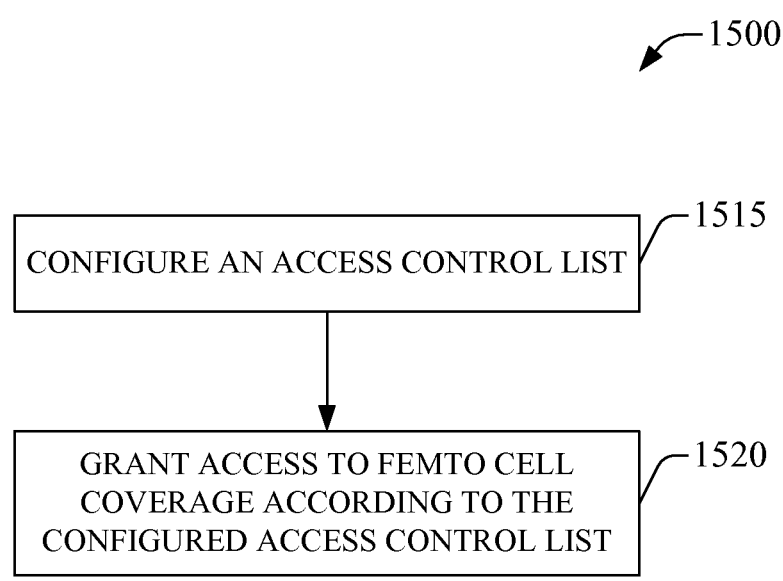
FIG. 15 presents a flowchart of an example method for managing access of subscribers and subscriber stations to femto cell coverage according to the disclosed subject matter.

FIG. 15 presents a flowchart of an example method 1500 for managing access of subscribers and subscriber stations to femto cell coverage. At act 1510 an access control list, or white list, for a femto cell is configured. In an aspect, configuration can be performed via a networked interface, interactively or automatically based at least in part on operation conditions of the femto cell; e.g., initial provisioning, capturing of wireless devices, responding to request for access, updating extant access control lists, and so forth. At act 1520, access to femto cell coverage is granted according to the configured access control list. In another aspect, the configured access control list can possess an associated profile that control logic for utilization of the access control list, via a set of parameters that determine conditions of access, type of access, etc.

Figure 16:
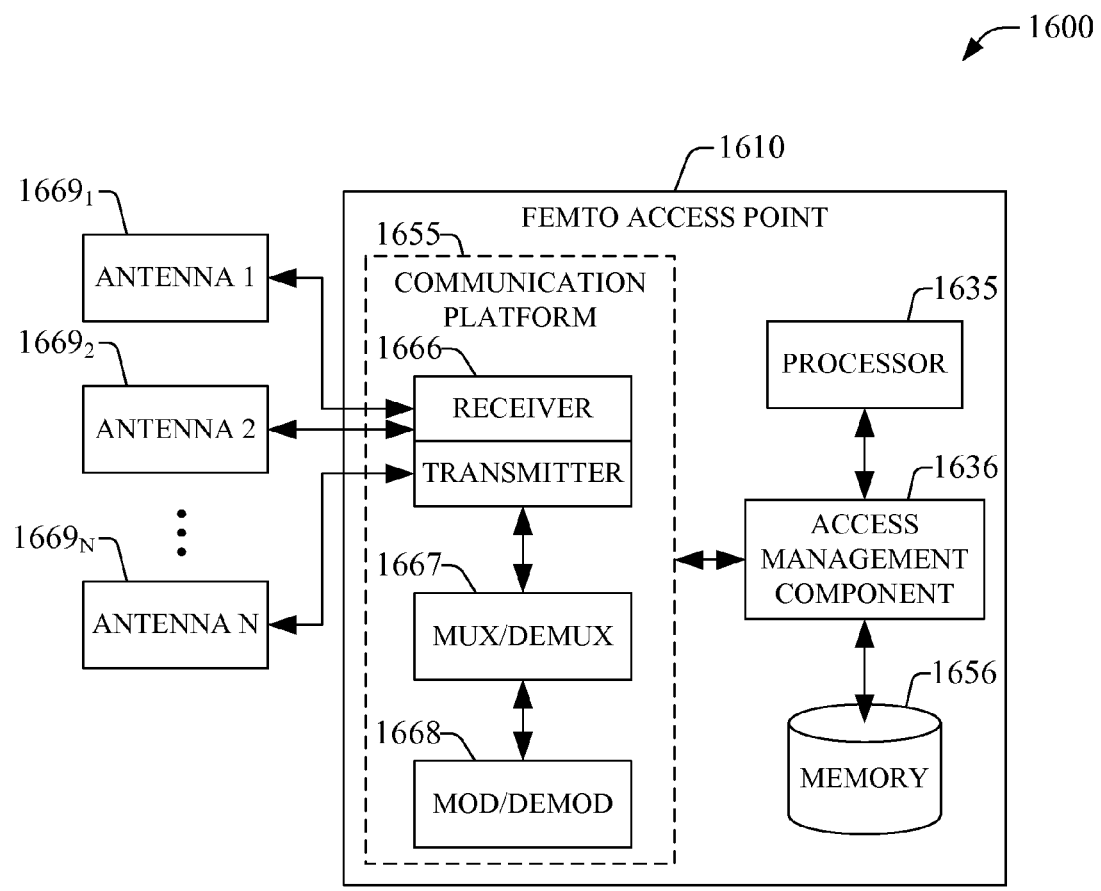
FIG. 16 is a block diagram of an example femto access point that operates in accordance with aspects disclosed in the subject specification.

FIG. 16 illustrates a block diagram of an example embodiment 1600 of a femto access point that can enable and exploit and manage femto coverage via access control list(s), or white list(s), in accordance with aspects described herein. Those skilled in the art will recognize that the specification also be implemented through program modules stored in a memory and executed by a processor, and/or other combination of hardware and software.

With respect to FIG. 16, in embodiment 1600, femto AP 1610 can receive and transmit signal(s) from and to wireless devices like macro and femto access points, access terminals, wireless ports and routers, and the like, through a set of antennas $1669_1$-$1669_N$. It should be appreciated that while antennas $1669_1$-$1669_N$ are a part of communication platform 1655, which comprises electronic components and associated circuitry that provides for processing and manipulation of received signal(s) and signal(s) to be transmitted. In an aspect, communication platform 1655 includes a receiver/transmitter 1666 that can convert signal from analog to digital upon reception, and from digital to analog upon transmission. In addition, receiver/transmitter 1666 can divide a single data stream into multiple, parallel data streams, or perform the reciprocal operation. Coupled to receiver/transmitter 1666 is a multiplexer/demultiplexer 1667 that facilitates manipulation of signal in time and frequency space. Electronic component 1667 can multiplex information (data/traffic and control/signaling) according to various multiplexing schemes such as time division multiplexing (TDM), frequency division multiplexing (FDM), orthogonal frequency division multiplexing (OFDM), code division multiplexing (CDM), space division multiplexing (SDM). In addition, mux/demux component 1667 can scramble and spread information (e.g., codes) according to substantially any code known in the art; e.g., Hadamard-Walsh codes, Baker codes, Kasami codes, polyphase codes, and so on. A modulator/demodulator 1668 is also a part of operational group 1625, and can modulate information according to multiple modulation techniques, such as frequency modulation, amplitude modulation (e.g., M-ary quadrature amplitude modulation (QAM), with M a positive integer), phase-shift keying (PSK), and the like.

Femto access point 1610 also includes a processor 1635 configured to confer functionality, at least partially, to substantially any electronic component in the femto access point 1610. In particular, processor 1635 can facilitate access management component 1636 to supply fixed differentiated QoS in accordance to aspects disclosed herein. In addition, processor 1635 can facilitate operations on data (e.g., symbols, bits, or chips) for multiplexing/demultiplexing, such as effecting direct and inverse fast Fourier transforms, selection of modulation rates, selection of data packet formats, interpacket times, etc. A memory 1656 can store data structures, code instructions, system or device information like policies and specifications, code sequences for scrambling, spreading and pilot transmission, floor plan configuration, access point deployment and frequency plans, scheduling policies, and so on.

In embodiment 1600, processor 1635 is coupled to the memory 1655 in order to store and retrieve information necessary to operate and/or confer functionality to communication platform 1655, access management component 1636, and other operational aspects of femto access point 1610.

As it employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Processors can exploit nano-scale architectures such as, but not limited to, molecular and quantum-dot based transistors, switches and gates, in order to optimize space usage or enhance performance of user equipment. A processor may also be implemented as a combination of computing processing units.

In the subject specification, terms such as "data store," data storage," "database," and substantially any other information storage component relevant to operation and functionality of a component, refer to "memory components," or entities embodied in a "memory" or components comprising the memory. For example, information relevant to operation of various components described in the disclosed subject matter, and that can be stored in a memory, can comprise, but is not limited to comprising, subscriber information; femto cell configuration (e.g., devices served by a femto AP; access control lists, or white lists) or service policies and specifications; privacy policies; and so forth. It will be appreciated that the memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), or flash memory. Volatile memory can include random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). Additionally, the disclosed memory components of systems or methods herein are intended to comprise, without being limited to comprising, these and any other suitable types of memory.

Various aspects or features described herein may be implemented as a method, apparatus, or article of manufacture using standard programming and/or engineering techniques. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick, key drive . . . ).

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

Moreover, terms like "user equipment," "mobile station," "mobile," subscriber station," "access terminal," "terminal," "handset," and similar terminology, refer to a wireless device utilized by a subscriber or user of a wireless communication service to receive or convey data, control, voice, video, sound, gaming, or substantially any data-stream or signaling-stream. The foregoing terms are utilized interchangeably in the subject specification and related drawings. Likewise, the terms "access point," "base station," "Node B." "evolved Node B," and the like, are utilized interchangeably in the subject application, and refer to a wireless network component or appliance that serves and receives data, control, voice, video, sound, gaming, or substantially any data-stream or signaling-stream from a set of subscriber stations. Data and signaling streams can be packetized or frame-based flows.

The following abbreviations and terms are relevant to the subject specification.

3G Third Generation
3GPP Third Generation Partnership Project
AGPS Assisted GPS
AP Access Point
ADSL Asymmetric Digital Subscriber Line
AWS Advanced Wireless Services
BRAS Broadband Remote Access Server
BTA Basic Trading Area
CN Core Network
CS Circuit-Switched
CSCF Call Session Control Function
CPE Customer Premise Equipment
CPN Customer Premise Network
DHCP Dynamic Host Configuration Protocol
DSL Digital Subscriber Line
DSLAM Digital Subscriber Line Access Multiplexer
E911 Enhanced 911
FCC Federal Communications Commission
FL Forward Link
GGSN Gateway GPRS Service Node
GPRS General Packet Radio Service
GPS Global Positioning System
GW Gateway
HAP Home Access Point
HSS Home Subscriber Server
ISDN Integrated Services Digital Network
UE User Equipment
UTRAN Universal Terrestrial Radio Access Network
IMS IP Multimedia Subsystem
IP Internet Protocol
ISP Internet Service Provider
MSA Metropolitan Statistical Areas
MSISDN Mobile Subscriber ISDN Number
MTA Major Trading Areas
NAT Network Address Translation
NTP Network Time Protocol
O&M Operation and Maintenance
PC Personal Computer
PCS Personal Communications Service
PS Packet-Switched
PSTN Public Switched Telephone Network
RAN Radio Access Network
RBS Radio Base Station
RL Reverse Link
RNC Radio Network Controller
RSA Rural Service Area
SGSN Serving GPRS Support Node SIP Session Initiation Protocol
USSD Unstructured Supplementary Service Data
VPN Virtual Private Network
WAP Wireless Application Protocol
XDSL Asynchronous-DSL or Synchronous-DSL What has been described above includes examples of systems and methods that provide advantages of the subject innovation. It is, of course, not possible to describe every conceivable combination of components or methodologies for purposes of describing the claimed subject matter, but one of ordinary skill in the art may recognize that many further combinations and permutations of the claimed subject matter are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A method, comprising:
    populating, by a system comprising a processor, an access control data structure with timing data and logout data, wherein the timing data is indicative of a time period during which a user equipment is authorized to access a femto access point device and the logout data specifies when a logout procedure to disconnect the user equipment from the femto access point device is to be implemented;
    receiving, by a system comprising a processor, frequency data indicative of a frequency of adjusting the timing data, wherein the receiving comprises receiving the frequency data from the user equipment;
    monitoring, by the system, a set of applications accessed by the user equipment via the femto access point device during the time period; and
    based on the frequency data and in response to determining that information associated with the set of applications satisfies a defined criterion, modifying, by the system, the timing data to increase the time period during which the user equipment is authorized to access the femto access point device, wherein the modifying comprises modifying the timing data in response to verifying that permission data that authorizes the modifying has been received.

2. The method of claim 1, wherein the monitoring comprises determining type data indicative of a type of application of the set of applications accessed by the user equipment.

3. The method of claim 1, wherein the populating comprises populating the access control data structure with the timing data that specifies an implicit value of time.

4. The method of claim 1, further comprising:
    based on the frequency data and in response to determining that the information does not satisfy the defined criterion, modifying, by the system, the timing data to reduce the time period.

5. The method of claim 1, wherein the modifying comprises modifying the timing data independent of user intervention.

6. The method of claim 1, further comprising:
    configuring, by the system, the timing data to specify a time related event, comprising an emergency time period during which the user equipment is authorized to access the femto access point device.

7. The method of claim 1, wherein the access control data structure further comprises access data indicative of a number of access attempts that the user equipment is permitted to request and the method further comprises:
    based on the information associated with the set of applications, modifying, by the system, the access data to modify the number of access attempts that the user equipment is permitted to request.

8. The method of claim 1, wherein the access control data structure further comprises modality data indicative of a communication technology that the user equipment is permitted to utilize during a communication with the femto access point device and the method further comprises:
    based on the information associated with the set of applications, modifying, by the system, the modality data to modify the communication technology that the user equipment is permitted to utilize during the communication with the femto access point device.

9. The method of claim 1, wherein the time period is a first time period and the method further comprises:
    denying, by the system, access of the femto access point device by the user equipment during a second time period that is different from the first time period.

10. The method of claim 1, wherein the monitoring comprises monitoring the set of applications in view of policy data indicative of a defined policy.

11. The method of claim 1, wherein the monitoring comprises monitoring the set of applications in view of statistical data.

12. The method of claim 1, further comprising:
    based on the information associated with the set of applications, restricting, by the system, a communication between the user equipment and the femto access point device to a transmission of a set of text messages.

13. A system, comprising:
    a memory to store executable instructions; and
    a processor, coupled to the memory, that facilitates execution of the executable instructions to perform operations, comprising:
        populating an access control data structure with timing data and logout data, wherein the timing data is indicative of a time period during which a user equipment is allowed to access a femto access point device and the logout data specifies when a logout procedure that initiates a disconnection of the user equipment from the femto access point device is to be implemented,
        determining a set of applications accessed by the user equipment via the femto access point device during the time period based on a monitoring of femto cell activity of the user equipment, and
        based on configuration data received from the user equipment and in response to determining that type data indicative of a type of an application of the set of applications satisfies a defined type criterion and that permission data that authorizes a modification to the timing data has been received, increasing the time period, wherein the configuration data comprises frequency data representing a frequency of adjusting the timing data.

14. The system of claim 13, wherein the operations further comprise:
    based on the configuration data and in response to determining that the type data does not satisfy the defined type criterion, decreasing the time period.

15. The system of claim 13, wherein the increasing comprises increasing the time period independent of user intervention.

16. A computer-readable storage device having executable instructions stored thereon that, in response to execution, cause a system comprising a processor to perform operations, comprising:
- configuring an access control data structure related to a femto access point device that specifies timing data indicative of a time period during which a user equipment is authorized to communicate with the femto access point device and that specifies logout data indicative of a duration when a logout procedure to facilitate a disconnection of the user equipment from the femto access point device is to be implemented;
- receiving, from the user equipment, frequency data indicative of a frequency of updating the timing data;
- determining an application accessed by the user equipment via the femto access point device during the time period; and
- based on the frequency data and in response to determining that classification data indicative of a type of the application satisfies a defined criterion, updating the timing data to increase the time period for which the user equipment is authorized to communicate with the femto access point device, wherein the updating comprises updating the timing data in response to verifying that permission data that authorizes the updating has been received.

17. The computer-readable storage device of claim 16, wherein the time period is a first time period and the operations further comprise:
- denying a communication between the user equipment and the femto access point device during a second time period that is different from the first time period.

18. The computer-readable storage device of claim 16, wherein the access control data structure further comprises modality data indicative of a communication technology that the user equipment is permitted to utilize to communicate with the femto access point device, the frequency data is first frequency data, the frequency is a first frequency, and the operations further comprise:
- receiving, from the user equipment, second frequency data indicative of a second frequency of updating the modality data; and
- based on the second frequency data and the classification data, modifying the modality data.

19. The computer-readable storage device of claim 16, wherein the access control data structure further comprises access data indicative of a number of access attempts that the user equipment is permitted to request and the operations further comprise:
- based on the classification data, modifying the access data to change the number of access attempts that the user equipment is permitted to request.

20. The computer-readable storage device of claim 16, wherein the operations further comprise:
- based on the frequency data and in response to determining that classification data does not satisfy the defined criterion, updating the timing data to decrease the time period for which the user equipment is authorized to communicate with the femto access point device.

* * * * *